United States Patent [19]

De Vries

[11] Patent Number: 4,623,662
[45] Date of Patent: * Nov. 18, 1986

[54] ANTIATHEROSCLEROTIC UREAS AND THIOUREAS

[75] Inventor: Vern G. De Vries, Ridgewood, N.J.

[73] Assignee: American Cyanamid Company, Stamford, Conn.

[*] Notice: The portion of the term of this patent subsequent to Jun. 7, 2000 has been disclaimed.

[21] Appl. No.: 737,360

[22] Filed: May 23, 1985

Related U.S. Application Data

[63] Continuation-in-part of Ser. No. 515,321, Jul. 19, 1983, abandoned, which is a continuation-in-part of Ser. No. 342,692, Jan. 26, 1982, abandoned.

[51] Int. Cl.$^4$ .................. A61K 31/175; C07C 127/19
[52] U.S. Cl. ..................... 514/596; 514/585; 514/586; 514/587; 514/588; 514/589; 514/597; 514/598; 564/49; 564/52
[58] Field of Search ............... 514/580, 586, 585, 587, 514/588, 589, 596, 597, 598; 564/49-52

[56] References Cited

U.S. PATENT DOCUMENTS

| | | | |
|---|---|---|---|
| 2,709,648 | 5/1955 | Ryker et al. | 564/53 |
| 2,867,520 | 1/1959 | Beaver et al. | 564/53 |
| 2,993,930 | 7/1961 | Chappelow | 564/55 |
| 3,326,663 | 6/1967 | Soloway et al. | 564/53 |
| 3,897,493 | 7/1975 | Teach | 564/48 |
| 4,010,281 | 3/1977 | Yamada et al. | 564/48 |
| 4,127,673 | 11/1978 | Yamada et al. | 564/53 |
| 4,387,105 | 7/1983 | De Vries et al. | 514/585 |
| 4,387,106 | 7/1983 | De Vries et al. | 514/598 |
| 4,397,868 | 8/1983 | De Vries | 514/598 |
| 4,405,644 | 9/1983 | Kabbe et al. | 564/52 |
| 4,473,579 | 9/1984 | De Vries et al. | 564/53 |

Primary Examiner—Leonard Schenkman
Assistant Examiner—Joseph A. Lipovsky
Attorney, Agent, or Firm—Edward A. Conroy, Jr.

[57] ABSTRACT

This invention is concerned with ureas and thioureas which may be represented by the formula:

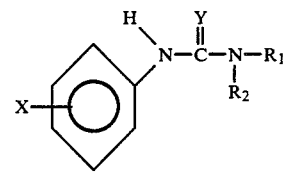

wherein X represents at least one substituent selected from the group consisting of ($C_1$-$C_4$)alkyl, ($C_1$-$C_4$)alkenyl, ($C_1$-$C_4$)alkynyl, phenoxy, mercapto, amino, ($C_1$-$C_4$)alkylamino, di-($C_1$-$C_4$)alkylamino, halo, trihalomethyl, ($C_1$-$C_4$)alkanoyl), benzoyl, ($C_1$-$C_4$)alkanamido, haloacetamido, nitro, cyano, carboxy, ($C_1$-$C_4$)carboalkoxy, carbamoyl, sulfamyl, methylenedioxy, phenyl, orthophenylene, tolyl, benzyl, halobenzyl, methylbenzyl; Y is selected from the group consisting of oxygen and sulfur; $R_1$ and $R_2$ are different and are independently selected from the group consisting of ($C_4$-$C_{12}$)alkyl, ($C_4$-$C_{12}$)alkenyl, ($C_4$-$C_{12}$)alkynyl, ($C_4$-$C_{12}$)cycloalkylalkyl, ($C_7$-$C_{14}$)aralkyl, and ($C_7$-$C_{14}$)aralkyl in which an aromatic ring bears at least one substituent selected from the group consisting of ($C_1$-$C_{10}$)alkyl, ($C_1$-$C_{10}$)alkoxy, phenoxy, benzyloxy, methylenedioxy, ($C_1$-$C_{14}$)alkylthio, phenyl, halo, trihalomethyl, adamantyl, ($C_1$-$C_4$)carboalkoxy, and nitro.

11 Claims, No Drawings

ANTIATHEROSCLEROTIC UREAS AND THIOUREAS

BACKGROUND OF THE INVENTION

This application is a continuation-in-part of my copending application Ser. No. 515,321, filed July 19, 1983, now abandoned, which in turn is a continuation-in-part of my abandoned application Ser. No. 342,692, filed Jan. 26, 1982, now abandoned.

This invention relates to new urea and thiourea compounds useful as pharmaceutical agents. The novel compounds of the present invention are antiatherosclerotic agents capable of ameliorating atherosclerosis by counteracting the formation or development of antheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

A variety of urea and thiourea compounds can be found in the literature, for example, in J. Med. Chem., 18: 1024 (1975); Chem. Absts., 95: 6758m (1981) and 91: 74631g (1979); U.S. Pat. Nos. 2,688,039; 3,335,142; 3,856,952; 3,903,130; 4,252,957; 4,405,644; and 4,460,607. The compounds found in the literature are disclosed as being useful herbicides, plant growth regulators, bactericides, pesticides, fungicides, algacides, photographic sensitizers, antihelmintics, sympatholytics, and antivirals. Those urea compounds found in U.S. Pat. Nos. 4,405,644 and 4,460,607 are disclosed as useful in inhibiting lipid absorption. There are, however, no literature references disclosing the urea and thiourea compounds of the present invention or their use in the treatment of atherosclerosis or hyperlipidemia.

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Atherosclerosis is the most common cause of ischemic heart disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plaques has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13: 429 (1974)] to contain a greater quantity of esterified as opposed to unesterified cholesterol than the surrounding undiseased arterial wall. The intracellular esterification of cholesterol with fatty acids is catalyzed by the enzyme Fatty acyl CoA: chloesterol acyl transferase or ACAT, and the accumulation and storage of cholesteryl esters in the arterial wall is associated with increased activity of this enzyme [Hashimoto and Dayton, Atheroscelerosis, 28: 447 (1977)]. In addition, cholesteryl esters are removed from cells at a slower rate than unesterified cholesterol [Bondjers and Bjorkerud, Atherosclerosis, 15: 273 (1972) and 22: 379 (1975)]. Thus, inhibition of the ACAT enzyme would diminish the rate of cholesterol esterification, decrease the accumulation and storage of cholesteryl esters in the arterial wall, and prevent or inhibit the formation and development of atheromatous lesions. The compounds of the present invention are very potent inhibitors of the ACAT enzyme. Thus, these compounds are useful for controlling and reducing the cholesteryl ester content of mammalian arterial walls and decreasing the accumulation and storage of cholesterol in the arterial walls of mammals. Further, the compounds of this invention inhibit the formation or development of atherosclerotic lesions in mammals.

The evidence that hyperlipidemia is one of the factors involved in coronary heart disease is very impressive. A most important study carried out in Framingham, Mass. in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown to carry the highest risk of coronary heart disease. The majority of patients with ischemic heart disease or peripheral vascular disease were found to have hyperlipoproteinemia, involving very low-density and/or low-density lipoproteins.

I have now found that certain members of this class of compounds can safely and effectively lower serum lipids in warm-blooded animals. Such action on serum lipids is considered to be very useful in the treatment of atherosclerosis. For some time, it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The compounds of this invention exhibit anti-atherosclerotic activity, and the invention should not be construed as limited to any particular mechanism of anti-atherosclerotic action.

SUMMARY OF THE INVENTION

This invention relates to new urea and thiourea compounds, their preparation, pharmaceutical compositions containing them, and their use in the treatment of atherosclerosis. More particularly, it is generically concerned with ureas and thioureas which may be represented by Formula I:

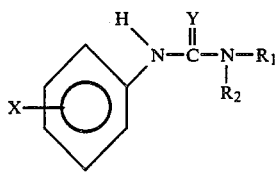

wherein X represents at least one substituent selected from the group consisting of $(C_1-C_4)$alkyl, $(C_1-C_4)$alkenyl, $(C_1-C_4)$alkynyl, phenoxy, mercapto, amino, $(C_1-C_4)$alkylamino, di-$(C_1-C_4)$alkylamino, halo, trihalomethyl, $(C_1-C_4)$alkanoyl, benzoyl, $(C_1-C_4)$alkanamido, haloacetamido, nitro, cyano, carboxy, $(C_1-C_4)$carboalkoxy, carbomyl, sulfamyl, methylenedioxy, phenyl, orthophenylene, tolyl, benzyl, halobenzyl, methylbenzyl, and the group:

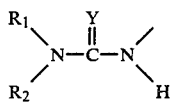

Y is selected from the group consisting of oxygen and sulfur; $R_1$ is selected from the group consisting of $(C_4-C_{12})$alkyl, $(C_4-C_{12})$alkenyl, $(C_4-C_{12})$alkynyl, $(C_4-C_{12})$cycloalkylalkyl, $(C_7-C_{14})$aralkyl, and $(C_7-C_{14})$aralkyl in which an aromatic ring bears at least one substituent selected from the group consisting of $(C_1-C_{10})$alkyl, $(C_1-C_{10})$alkoxy, phenoxy, benzyloxy, methylenedioxy, $(C_1-C_4)$alkylthio, phenyl, halo, trihalomethyl, adamantyl, $(C_1-C_4)$carboalkoxy, and nitro; and $R_2$ is not identical to $R^1$ and is selected from the group consisting of $(C_4-C_{12})$alkyl, $(C_4-C_{12})$alkenyl, $(C_4-C_{12})$alkynyl, $(C_4-C_{12})$cycloalkylalkyl, $(C_7-C_{14})$aralkyl, and $(C_7-C_{14})$aralkyl in which an aromatic ring bears at least one substituent selected from the group consisting of $(C_1-C_{10})$alkyl, $(C_1-C_{10})$alkoxy, phenoxy, benzyloxy, methylenedioxy, $(C_1-C_4)$alkylthio, phenyl, halo, trihalomethyl, adamantyl, $(C_1-C_4)$carboalkoxy, nitro, and A-Z wherein A is selected from the group consisting of $(C_2-C_{10})$alkylene, $(C_2-C_{10})$alkenylene, and $(C_2-C_{10})$alkynylene and Z is selected from the group consisting of carboxy, $(C_1-C_4)$carboalkoxy, carbamoyl, $(C_1-C_4)$perfluoroalkyl, (tri$(C_1-C_4)$alkyl)silyl, cyano, halo, mercapto, $(C_1-C_4)$alkylthio, hydroxy, $(C_1-C_4)$alkoxy, methylsulfonyloxy, $(C_1-C_4)$alkoxy, thienyl, furyl, and pyrimidinyl.

A preferred subgeneric group of ureas and thioureas with which this invention is concerned may be represented by Formula II:

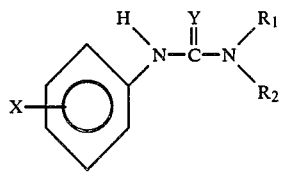

wherein X represents at least one substitutent selected from the group consisting of $(C_1-C_4)$alkyl, $(C_1-C_4)$alkenyl, $(C_1-C_4)$alkynyl, phenoxy, mercapto, amino, $(C_1-C_4)$alkylamino, di-$(C_1-C_4)$alkylamino, halo, trihalomethyl, $(C_1-C_4)$alkanoyl, benzoyl, $(C_1-C_4)$alkanamido, haloacetamido, nitro, cyano, carboxy, $(C_1-C_4)$carboalkoxy, carbamoyl, sulfamyl, methylenedioxy, phenyl, orthophenylene, tolyl, benzyl, halobenzyl, methylbenzyl; Y is selected from the group consisting of oxygen and sulfur; $R_1$ and $R_2$ are different and are independently selected from the group consisting of $(C_4-C_{12})$alkyl, $(C_4-C_{12})$alkenyl, $(C_4-C_{12})$alkynyl, $(C_4-C_{12})$cycloalkylalkyl, $(C_7-C_{14})$aralkyl, and $(C_7-C_{14})$aralkyl in which an aromatic ring bears at least one substituent selected from the group consisting of $(C_1-C_{10})$alkyl, $(C_1-C_{10})$alkoxy, phenoxy, benzyloxy, methylenedioxy, $(C_1-C_4)$alkylthio, phenyl, halo, trihalomethyl, adamantyl, $(C_1-C_4)$carboalkoxy, and nitro.

Preferred embodiments of the invention represented by Formula II are those in which Y is oxygen. More preferred are those in which X represents at least one $(C_1-C_4)$alkyl or halo substituent, $R_1$ is $(C_7-C_{14})$aralkyl or substituted $(C_7-C_{14})$aralkyl, and $R_2$ is $(C_4-C_{12})$alkyl. The most preferred are those in which X represents at least one methyl, chloro, or fluoro substituent.

Preferred specific embodiments involve trisubstituted ureas, for example:

1-Benzyl-1-(n-butyl)-3-(2,4-dimethylphenyl)urea
1Benzyl-1-(1,2-diphenylethyl)-3-(2,4-dimethylphenyl)urea
1-(2-Fluorobenzyl)-1-(2-methoxybenzyl)-3-(2,4-dimethylphenyl)urea
1-(n-Butyl)-1-(4-hexyloxybenzyl)-3-(2,4-dimethylphenyl)urea
1-Benzyl-1(4-n-butylbenzyl)-3-(2,4-dimethylphenyl)urea
1-Benzyl-1-(4-n-butylbenzyl)-3-(2,4,6-trimethylphenyl)urea
1-(n-Heptyl)-1-(4-n-butylbenzyl)-3-(2,4-dimethylphenyl)urea
1-(n-Heptyl)-1-(4-n-butylbenzyl)-3-(2,4,5-trimethylphenyl)urea
1-(n-Heptyl)-1-(4-butyloxybenzyl)-3-(2,4-dimethylphenyl)urea
1-(n-Heptyl)-1-(4-butyloxybenzyl)-3-(2,4,5-trimethylphenyl)urea
1-Benzyl-1-(4-butyloxybenzyl)-3-(2,4-dimethylphenyl)urea
1-Benzyl-1-(4butyloxybenzyl)-3-(2,4,5-trimethylphenyl)urea
1-Benzyl-1-(4-n-butylbenzyl)-3-(2,4,5-trimethylphenyl)urea
1-(n-Heptyl)-1-(4-n-butoxybenzyl)-3-(2,4,6-trichlorophenyl)urea
1-Benzyl-1-(4-n-butoxybenzyl)-3-(2,4,6-trichlorophenyl)urea
1-(n-Heptyl)-1-(4-n-butylbenzyl)-3-(2,4,6-trichlorophenyl)urea
1-Benzyl-1-(4-n-butylbenzyl)-3-(2-methyl-4-chlorophenyl)urea
1-(n-Heptyl)-1-(4-n-butoxybenzyl)-3-(2,4-difluorophenyl)urea
1-(n-Heptyl)-1-(4-n-butoxybenzyl)-3-(2-methyl-4-chlorophenyl)urea
1-(n-Heptyl)-1-(4-n-butylbenzyl)-3-(2-methyl-4-chlorophenyl)urea
1-(n-Heptyl)-1-(4-n-butylbenzyl)-3-(2,4-difluorophenyl)urea
1-(n-Heptyl)-1-(4-n-butylbenzyl)-3-(2-methylphenyl)urea
1-(n-Heptyl)-1-(2-phenylethyl)-3-(2,4-dimethylphenyl)urea
1-(4-Chlorobenzyl)-1-(1-naphthylmethyl)-3-(2,4,6-trichlorophenyl)urea 1-(4-Chlorobenzyl)-1-(1-naphthylmethyl)-3-(2-methyl-4-chlorophenyl)urea 1-(4-Chlorobenzyl)-1-(1-naphthylmethyl)-3-(2,4-difluorophenyl)urea 1-Benzyl-1-[2-phenyl-1-(4-benzyloxyphenyl)ethyl]-3-(2,4-difluorophenyl)urea 1-Benzyl-1-(4-n-butoxybenzyl)-3-(2,4-difluorophenyl)urea 1-(2-Furanylmethyl)-1-heptyl-3-(2,4,5-trimethylphenyl)urea 1-(2-Furanylmethyl)-1-heptyl-3-(2,4,6-trichlorophenyl)urea 1-Heptyl-1-(2-thienylmethyl)-3-(2,4,5-trimethylphenyl)urea 1-Heptyl-1-(2-thienylmethyl)-3-(2,4,6-trichlorophenyl)urea 1-[(4-Butoxyphenyl)methyl]-1-(2-thienylmethyl)-3-(2,4,5-trimethylphenyl)urea 1-[(4-Butylphenyl)methyl]-1-(6-cyanohexyl)-3-(2,4,5-trimethylphenyl)urea 1-[(4-Butylphenyl)methyl]-1-(6-chlorohexyl)-3-(2,4,5-trimethylphenyl)urea 1-[(4-Butylphenyl)methyl]-1-(6-chlorohexyl)-3-(4-chloro-2-methylphenyl)urea 1-[(4-Butylphenyl)methyl]-1-(6-hydroxyhexyl)-3-(2,4,6-trichlorophenyl)urea 1-[(4-Butylphenyl)methyl]-1-(6-cyanohexyl)-3-(2,4,6-trichlorophenyl)urea 1-[(4-Butylphenyl)methyl]-1-(6-chlorohexyl)-3-(2,4,6-trichlorophenyl)urea 1-(4-Phenylbenzyl)-1-(3,4-dichlorobenzyl)-3-(2,4-dimethylphenyl)urea 1-(3,4-Dimethylbenzyl)-1-(2-chlorobenzyl)-3-(2,4-dimethylphenyl)urea 1-(3,3-Dimethylbutyl)-1-[4-(n-butyl)benzyl]-3-(4-chloro-2-methylphenyl)urea 1-(3,3-Dimethylbutyl)-1-[4-(n-butoxy)benzyl]-3-(4-chloro-2-methylphenyl)urea 1-(3,3-Dimethylbutyl)-1-[4-(n-butoxy)benzyl]-3-(2,4,6-trichlorophenyl)urea 1-(3,3-Dimethylbutyl)-1-[4-(n-butoxy)benzyl]-3-(2,4-difluorophenyl)urea 1-(3,3-Dimethylbutyl)-1-[4-(n-butyl)benzyl]-3-(2,4-difluorophenyl)urea 1-(3,3-Dimethylbutyl)-1-[4-(n-butyl)benzyl]-3-(2,4,6-trichlorophenyl)urea 1-(5,5-Dimethylhexyl)-1-[4-(n-butyl)benzyl]-3-(4-chloro-2-methylphenyl)urea 1-(3,3-Dimethylbutyl)-1[4-(2,2-dimethylpropyl)benzyl]-3-(2,4-difluorophenyl)urea 1(3,3-Dimethylbutyl)-1-[4-(2,2-dimethylpropyl)benzyl]-3-(4-chloro-2-methylphenyl)urea 1-(3,3-Dimethylbutyl)-1-[4-(2,2-dimethylpropyl)benzyl]-3-(2,4,6-trichlorophenyl)urea 1-(3,3-Dimethylbutyl)-1-[4-(n-butyl)benzyl]-3-(4-chloro-2,6-dimethylphenyl)urea 1-(3,3-Dimethylbutyl)-1-(4-chlorobenzyl)-3-(4-chloro-2,6-dimethylphenyl)urea 1-(n-Heptyl)-1-[4-(n-butyl)benzyl]-3-(4-chloro-2,6-dimethylphenyl)urea 1-(3,3-Dimethylbutyl)-1-[4-(2,2-dimethylpropyl)benzyl]-3-(4-chloro-2,6-dimethylphenyl)urea 1-(n-Heptyl)-1-[4-(n-butyl)benzyl]-3-(4-chloro-2,5-dimethylphenyl)urea 1-(3,3-Dimethylbutyl)-1-(benzyl)-3-(4-chloro-2,5-dimethylphenyl)urea 1-(n-Heptyl)-1-[4-(2,2-dimethylpropyl)phenylmethyl]-3-(2,4-difluorophenyl)urea 1-(n-Heptyl)-1-[4-(2,2-dimethylpropyl)phenylmethyl]-3-(4-chloro-2,6-dimethylphenyl)urea 1-(n-Heptyl)-1-[4-(2,2-dimethylpropyl)phenylmethyl]-3-(2,4,6-trifluorophenyl)urea This invention also relates to a method of treating atherosclerosis in mammals which comprises administering to said mammal an effective amount of a compound as recited above.

This invention also relates to a method of reducing the cholesterol content of the arterial walls of mammals which comprises administering to said mammal an effective amount of a compound as recited above.

This invention also relates to a method of treating hyperlipidemia in mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to pharmaceutical compositions which comprise an effective antiatherosclerotic amount of a compound as recited above in association with a pharmaceutically acceptable carrier.

Finally, this invention relates to processes for preparing compounds as recited above. One process especially useful for the preparation of ureas and thioureas of Formula I involves reacting an arylisocyanate or arylisothiocyanate of Formula III with a secondary amine of Formula IV, wherein X, Y, $R_1$, and $R_2$ are as defined above.

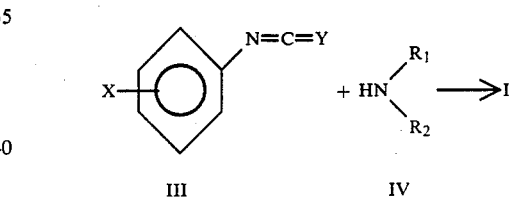

A second process for the preparation of ureas and thioureas of Formula I involves reacting a compound of Formula V; wherein E and B are leaving groups, which may be the same or different, selected from the group consisting of halo, ($C_1$–$C_4$)alkoxy, ($C_1$–$C_4$)alkylthio, phenoxy, 4-chlorophenoxy, and 4-nitrophenoxy; with a secondary amine of Formula IV to yield an intermediate of Formula VI and then reacting the intermediate with an arylamine of Formula VII, wherein X, Y, $R_1$, and $R_2$ are as defined above.

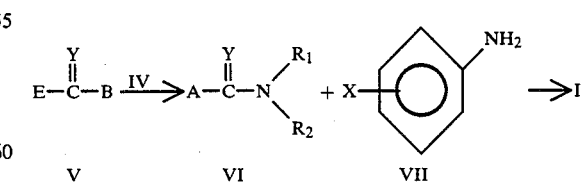

A third process for the preparation of ureas and thioureas of Formula I involves reacting a compound of Formula V with an arylamine of Formula VII to yield an intermediate of Formula VIII, wherein X, Y, E, and B are as defined above, and then reacting this intermediate with a secondary amine of Formula IV.

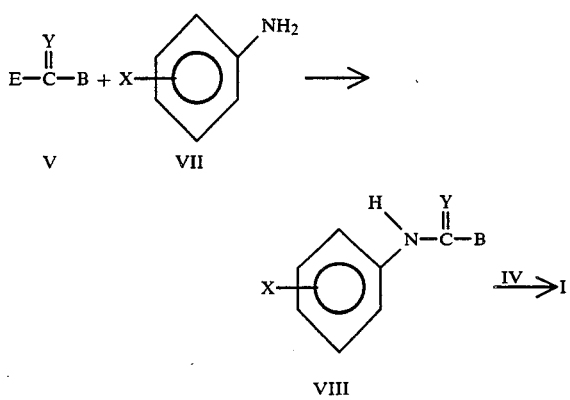

DETAILED DESCRIPTION OF THE INVENTION

Many of the novel ureas and thioureas of this invention are prepared by reacting arylisocyanates and arylisothiocyanates with secondary amines. These reactions may be performed in aprotic solvents such as hexane, diethyl ether, toluene, tetrahydrofuran, and the like at temperatures from room temperature or below up to the boiling point of the solvent used. The ureas and thioureas are isolated by filtration or by evaporation of the solvent, and they may be purified by recrystallization, absorption chromatography, or distillation under reduced pressure. Examples of this process are the reaction of 2,4-dimethylphenylisocyanate with N-benzyl-N-(n-butyl)amine to yield 1-benzyl-1-(n-butyl)-3-(2,4-dimethylphenyl)urea and the reaction of 6-[[(4-butylphenyl)methyl]amino]-1-hexanol with 2,4-dimethylphenyl isocyanate in hexane at room temperature to yield 1-[(4-butylphenyl)methyl]-3-(2,4-dimethylphenyl)-1-(6-hydroxyhexyl)urea.

Many of the secondary amines required for the synthesis of the ureas and thioureas of this invention are prepared by reductions of the corresponding amides. Reagents used for these reductions included diborane, lithium aluminum hydride, and sodium dihydrobis(2-methoxyethoxy)aluminate. Examples of this reaction are the syntheses of: 6-[[(4-butylphenyl)methyl]amino]--hexanol from 4-butyl-N-(6-hydroxyhexyl)benzamide by treatment with 1M borane-tetrahydrofuran complex in tetrahydrofuran; 4-butyl-N-[5-(trimethylsilyl)pentyl]benzenemethanamine from N-[(4-butylphenyl)methyl]-5-(trimethylsilyl)pentanamide by treatment with lithium aluminum hydride in tetrahydrofuran; 3,3-dimethylbutyl-2-thiophenemethanamine from 3,3-dimethylbutyl-2-thiophenecarboxamide by treatment with Vitride ® T [sodium dihydrobis(2-methoxyethoxy)aluminate (70% solution in toluene)]; and N-(n-butyl)-2-chlorobenzylamine by diborane reduction of N-(n-butyl)-2-chlorobenzamide.

Certain of the amides required by these reductions are prepared by acylation of primary amines with carboxylic acids by methods well known to those skilled in the art, for example, by conversion of the carboxylic acid to the corresponding carboxylic acid chloride using thionyl chloride and then reacting the acid chloride with the primary amine in the presence of a base. One method especially useful for this transformation is the boron trifluoride etherate catalyzed reaction of a carboxylic acid with a primary amine. An example of this transformation is the boron trifluoride etherate catalyzed acylation of 2-chlorobenzylamine with 3-methoxyphenylacetic acid to yield N-(2-chlorobenzyl)-3-methoxyphenylacetamide. Another example of this reaction is the preparation of 4-butyl-N-(6-hydroxyhexyl)benzamide from 6-amino-1-hexanol, triethylamine and p-butylbenzoyl chloride in dichloromethane.

Certain of the novel ureas and thioureas of this invention are prepared by reacting arylamines with activated derivatives of carbonic acid such as phosgene or thiophosgene to yield an intermediate, for instance, an arylcarbamyl chloride. This intermediate is then reacted with a secondary amine to yield the urea or thiourea. The preparation of this intermediate is conducted in an aprotic solvent such as tetrahydrofuran, toluene, or xylene at temperatures from about room temperature up to the boiling point of the solvent in the presence of a base, for example, N,N-dimethylaniline. The intermediate is then reacted with an arylamine in an aprotic solvent such as dimethylacetamide in the presence of a base such as sodium hydride at temperatures from about room temperature up to the boiling point of the solvent used.

Other of the novel ureas and thioureas of this invention are prepared by reacting arylamines with activated derivatives of carbonic acid such as phosgene or thiophosgene to yield an intermediate, for instance, an arylcarbamyl chloride. This intermediate is then reacted with a secondary amine to yield the urea or thiourea. The preparation of this intermediate is conducted in an aprotic solvent such as toluene or xylene at temperatures from about room temperature up to the boiling point of the solvent in the presence of a base, for example, N,N-dimethylaniline.

The intermediate is then reacted with a secondary amine in an aprotic solvent such as toluene at temperatures from room temperature or below up to the boiling point of the solvent. An example of this process is the reaction of 2,4-difluoroaniline with phenyl chloroformate to yield the intermediate phenyl N-(2,4-difluorophenyl)carbamate which is then reacted with N-(4-butylphenyl)-N-(6-hydroxyhexyl)amine to yield 1-(4-n-butylphenyl)-3-(2,4-difluorophenyl)-1-(6-hydroxyhexyl)urea.

The ureas and thioureas of this invention which contain carboxy groups are prepared by alkaline hydrolysis of the corresponding carboalkoxy ureas and thioureas, prepared by the synthetic methods described above. Likewise, those which contain hydroxy, mercapto, or amino groups are prepared by alkaline hydrolysis of the corresponding O-acetyl, S-acetyl, and N-acetyl ureas and thioureas, respectively, the latter also having been obtained by the urea and thiourea syntheses described above. Alternatively, ureas and thioureas containing hydroxy groups are prepared by cleavage of the corresponding methoxy compounds using Lewis acids such as boron tribromide.

One of the intermediates, 5-(trimethylsilyl)pentanoic acid, was prepared by reaction of the Grignard reagent derived from bromomethyltrimethylsilane with the magnesium salt of 4-bromobutyric acid.

The ureas and thioureas of the present invention, in general, are obtained as crystalline solids or distillable liquids. They are characterized by distinct melting and boiling points and unique spectra. They are appreciably soluble in organic solvents but generally less soluble in water. Those compounds which contain carboxylic acid groups may be converted to their alkali metal and alkaline earth salts by treatment with the appropriate metal hydroxides, and those which contain amino groups may be converted to their ammonium salts by treatment with organic or mineral acids. Both of these types of salts exhibit increased water solubility.

The preparation and properties of the compounds of this invention will be described in greater detail in conjunction with the specific examples shown below.

The compounds of the present invention were assayed for two types of biological activity related to their potential use as antiatherosclerotic agents. Compounds were tested in vitro for the ability to inhibit the enzyme fatty acyl CoA: cholesterol acyl transferase (ACAT) and in vivo for serum hypolipidemic activity as meausred by the ability to inhibit lipid absorption in rats.

The compounds were tested for their ability to inhibit ACAT according to the following procedure: rat adrenals were homogenized in 0.2M monobasic potassium phosphate buffer, pH 7.4, and centrifuged at 1,000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of bovine serum albumin (50 mg/ml), 3 parts of test compound (final concentration 5.2 μg/ml), and 500 parts of buffer was preincubated at 37° C. for 10 minutes. After treatment with 20 parts of oleoyl CoA ($^{14}$C–0.4 μCi), the mixture was incubated at 37° C. for 10 minutes. A control mixture, omitting the test compound, was prepared and treated in the same manner. The lipids from the incubation mixture was extracted into an organic solvent and separated by thin-layer chromatography. The cholesteryl ester fraction was counted in a scintillation counter. This procedure is a modification of that described by Hashimoto, et al., Life Scie., 12 (Part II), 1–12 (1973).

Compounds which produced statistically significant inhibition of the ACAT enzyme are considered to be active. The results of this test on representative compounds of this invention appear in Table I.

TABLE 1

| Compound | % Inhibition |
| --- | --- |
| 1-Benzyl-1-(n-butyl)-3-(3-methylphenyl)-urea | 92.3 |
| 1-Benzyl-1-(n-butyl)-3-(3-trifluoromethylphenyl)urea | 85.7 |
| 1-Benzyl-1-(n-butyl)-3-(3,5-dichlorophenyl)urea | 90.7 |
| 1-Benzyl-1-(n-butyl)-3-(3,4-dichlorophenyl)urea | 95.9 |
| 1-Benzyl-1-(n-butyl)-3-(3-chlorophenyl)-urea | 88.6 |
| 1-Benzyl-1-(n-butyl)-3-(2,4-dimethylphenyl)urea | 91.3 |
| 1-Benzyl-1-(n-butyl)-3-(2-methylphenyl)-urea | 78.8 |
| 1-Benzyl-1 (n-butyl)-3-(4-methylphenyl)-urea | 78.0 |
| 1-Benzyl-1-(n-butyl)-3-(2,3-dimethylphenyl)urea | 85.8 |
| 1-Benzyl-1-(n-butyl)-3-(2,5-dimethylphenyl)urea | 92.7 |
| 1-Benzyl-1-(n-butyl)-3-(2,6-dimethylphenyl)urea | 83.1 |
| 1-Benzyl-1-(n-butyl)-3-(3,5-dimethylphenyl)urea | 94.2 |
| 1-Benzyl-1-[1-(3-methoxyphenyl)-2-phenylethyl]-3-(2,4-dimethylphenyl)urea | 86.4 |
| 1-Benzyl-1-[1-(4-benzyloxyphenyl)-2-phenylethyl]-3-(2,4-dimethylphenyl)urea | 93.0 |

TABLE 1-continued

| Compound | % Inhibition |
| --- | --- |
| 1-Benzyl-1-(1,2-diphenylethyl)-3-(2,4-dimethylphenyl)urea | 95.0 |
| 1-Benzyl-1-(n-butyl)-3-(3,4-dimethylphenyl)urea | 87.1 |
| 1-Benzyl-1-[1-(3-methoxyphenyl)-2-phenylethyl]-3-(3-trifluoromethylphenyl)urea | 88.1 |
| 1-Benzyl-1-(n-butyl)-3-(3-chloro-2-methoxyphenyl)urea | 84.5 |
| 1-Benzyl-1-(n-butyl)-3-(5-chloro-2-methoxyphenyl)urea | 80.6 |
| 1-Benzyl-1-(n-butyl)-3-phenyl thiourea | 82.4 |
| 1-(n-Butyl)-1-(2-fluorobenzyl)-3-(2,4-dimethylphenyl)urea | 83.6 |
| 1-(n-Butyl)-1-(4-fluorobenzyl)-3-(2,4-dimethylphenyl)urea | 80.6 |
| 1-(n-Butyl)-1-(2-chlorobenzyl)-3-(2,4-dimethylphenyl)urea | 95.5 |
| 1-(n-Butyl)-1-(2,6-dichlorobenzyl)-3-(2,4-dimethylphenyl)urea | 74.5 |
| 1-(n-Butyl)-1-(4-bromobenzyl)-3-(2,4-dimethylphenyl)urea | 81.0 |
| 1-(n-Butyl)-1-[4-(n-butyl)benzyl]-3-(2,4-dimethylphenyl)urea | 94.4 |
| 1-(n-Butyl)-1-(4-methylbenzyl)-3-(2,4-dimethylphenyl)urea | 96.7 |
| 1-(n-Butyl)-1-(4-tert-butylbenzyl)-3-(2,4-dimethylphenyl)urea | 96.4 |
| 1-(n-Butyl)-1-(4-chlorobenzyl)-3-(2,4-dimethylphenyl)urea | 94.6 |
| 1-(n-Butyl)-1-(4-methoxybenzyl)-3-(2,4-dimethylphenyl)urea | 94.2 |
| 1-(n-Butyl)-1-(3,4-methylenedioxybenzyl)-3-(2,4-dimethylphenyl)urea | 88.2 |
| 1-(n-Butyl)-1-(4-trifluoromethylbenzyl)-3-(2,4-dimethylphenyl)urea | 93.3 |
| 1-(n-Butyl)-1-(4-phenylbenzyl)-3-(2,4-dimethylphenyl)urea | 97.1 |
| 1-(n-Decyl)-1-benzyl-3-(2,4-dimethylphenyl)urea | 96.1 |
| 1-(n-Butyl)-1-(2-phenylethyl)-3-(2,4-dimethylphenyl)urea | 87.9 |
| 1-(n-Butyl)-1-[2-(4-fluorophenyl)ethyl]-3-(2,4-dimethylphenyl)urea | 96.1 |
| 1-(n-Butyl)-1-[2-(4-chlorophenyl)ethyl]-3-(2,4-dimethylphenyl)urea | 93.3 |
| 1-(n-Butyl)-1-[2-(3-methoxyphenyl)ethy]-3-(2,4-dimethylphenyl)urea | 98.3 |
| 1-(n-Butyl)-1-(3-phenylpropyl)-3-(2,4-dimethylphenyl)urea | 97.4 |
| 1-(n-Butyl)-1-benzyl-3-(2,4,6-trimethylphenyl)urea | 75.8 |
| 1-(n-Butyl)-1-[4-(n-hexyl)benzyl]-3-(2,4-dimethylphenyl)urea | 93.8 |
| 1-(n-Tetradecyl)-1-benzyl-3-(2,4-dimethylphenyl)urea | 80.3 |
| 1-(n-Butyl)-1-[2-(3-bromophenyl)ethyl]-3-(2,4-dimethylphenyl)urea | 97.0 |
| 1-[2-(3,4-Dimethoxyphenyl)ethyl]-1-(3-chloro-4-methylbenzyl)-3-(2,4-dimethylphenyl)urea | 53.3 |
| 1-[2-(2-Methylphenyl)ethyl]-1-(4-bromobenzyl)-3-(2,4-dimethylphenyl)urea | 29.2 |
| 1-[2-(3-Trifluoromethylphenyl)ethyl]-1-(2-chlorobenzyl)-3-(2,4-dimethylphenyl)urea | 7.8 |
| 1-(2-Fluorobenzyl)-1-(2-methoxybenzyl)-3-(2,4-dimethylphenyl)urea | 41.5 |
| 1-[2-(3,4-Dimethoxyphenyl)ethyl]-1-(4-fluorobenzyl)-3-(2,4-dimethylphenyl)urea | 57.4 |
| 1-[2-(4-Ethoxyphenyl)ethyl]-1-(2,4-dimethylbenzyl)-3-(2,4-dimethylphenyl)urea | 34.9 |
| 1-[2-(3-Methylphenyl)ethyl]-1-(3-nitrobenzyl)-3-(2,4-dimethylphenyl)urea | 95.7 |
| 1-[2-(2,5-Dimethoxyphenyl)ethyl]-1-(3-chlorobenzyl)-3-(2,4-dimethylphenyl)urea | 97.1 |
| 1-(n-Butyl)-1-(2-methyl-2,2-diphenyl)ethyl-3-(2,4-dimethylphenyl)urea | 97.4 |
| 1-(n-Butyl)-1-(4-hexyloxybenzyl)-3-(2,4,6-trimethylphenyl)urea | 97.1 |
| 1-(n-Butyl)-1-(4-heptyloxybenzyl)-3- | 97.3 |

TABLE 1-continued

| Compound | % Inhibition |
|---|---|
| 1-(n-Butyl)-1-benzyl-3-(4-trifluoroacetylamino-3,5-dichlorophenyl)urea | 87.8 |
| 1-Benzyl-1-(4-n-butylbenzyl)-3-(2,4-dimethylphenyl)urea | 91.9 |
| 1-Benzyl-1-(4-n-butylbenzyl)-3-(2,4,6-trimethylphenyl)urea | 92.8 |
| 1-Benzyl-1-(4-n-butylbenzyl)-3-(4-n-butylphenyl)urea | 92.0 |
| 1-Benzyl-1-(4-n-butylbenzyl)-3-(4-phenoxyphenyl)urea | 93.5 |
| 1-(n-Heptyl)-1-(4-n-butylbenzyl)-3-(2,4-dimethylphenyl)urea | 94.8 |
| 1-(n-Heptyl)-1-(4-n-butylbenzyl)-3-(2,4,5-trimethylphenyl)urea | 95.3 |
| 1-Benzyl-1-[2-phenyl-1-(4-benzyloxyphenyl)ethyl]-3-(2,4,5-trimethylphenyl)urea | 93.7 |
| 1-(n-Heptyl)-1-(4-butyloxybenzyl)-3-(2,4-dimethylphenyl)urea | 94.6 |
| 1-(n-Heptyl)-1-(4-butyloxybenzyl)-3-(2,4,5-trimethylphenyl)urea | 95.6 |
| 1-Benzyl-1-(4-butyloxybenzyl)-3-(2,4-dimethylphenyl)urea | 91.7 |
| 1-Benzyl-1-(4-butyloxybenzyl)-3-(2,4,5-trimethylphenyl)urea | 95.8 |
| 1-Benzyl-1-(4-n-butylbenzyl)-3-(2,4,5-trimethylphenyl)urea | 90.5 |
| 1-Benzyl-1[2-phenyl-1-(4-benzyloxyphenylethyl]-3-(2,4,6-trimethylphenyl)urea | 90.0 |
| 1-(n-Heptyl)-1-(4-n-butoxybenzyl)-3-(2,4,6-trichlorophenyl)urea | 90.0 |
| 1-(n-Heptyl)-(4-n-butoxybenzyl)-3-(2,4-dichlorophenyl)urea | 79.9 |
| 1-(n-Heptyl)-(4-n-butoxybenzyl)-3-(2-trifluoromethyl-4-chlorophenyl)urea | 89.4 |
| 1-Benzyl-1-(4-n-butoxybenzyl)-3-(2,4,6-trichlorophenyl)urea | 95.2 |
| 1-Benzyl-1-(4-n-butoxybenzyl)-3-(2,4-dichlorophenyl)urea | 80.0 |
| 1-Benzyl-1-(4-n-butoxybenzyl)-3-(2-trifluoromethyl-4-chlorophenyl)urea | 85.0 |
| 1-(n-Heptyl)-1-(4-n-butoxybenzyl)-3-(3-trifluoromethylphenyl)urea | 82.4 |
| 1-(n-Benzyl-1-(4-n-butoxybenzyl)-3-(3-trifluoromethylphenyl)urea | 87.0 |
| 1-(n-Heptyl)-1-(4-n-butylbenzyl)-3-(2,4-dichlorophenyl)urea | 80.0 |
| 1-(n-Heptyl)-1-(4-n-butylbenzyl)-3-(2-trifluoromethyl-4-chlorophenyl)urea. | 90.0 |
| 1-(n-Heptyl)-1-(4-n-butylbenzyl)-3-(2,4,6-trichlorophenyl)urea | 90.0 |
| 1-(n-Heptyl)-1-(4-n-butylbenzyl)-3-(3-trifluoromethylphenyl)urea | 85.0 |
| 1-(n-Heptyl)-1-(4-n-butylbenzyl)-3-(2,4,5-trichlorophenyl)urea | 46.5 |
| 1-Benzyl-1-(4-n-butylbenzyl)-3-(2-methyl-4-chlorophenyl)urea | 94.3 |
| 1-(n-Heptyl)-1-(4-n-butoxybenzyl)-3-(2,4-difluorophenyl)urea | 82.7 |
| 1-(n-Heptyl)-1-(4-n-butoxybenzyl)-3-(2-methyl-4-chlorophenyl)urea | 91.7 |
| 1-(n-Heptyl)-1-(2-furyl)-3-(2,4,5-trimethylphenyl)urea | 93.8 |
| 1-(n-Heptyl)-1-(2-furyl)-3-(2,4,6-trichlorophenyl)urea | 96.1 |
| 1-(n-Heptyl)-1-(4-n-butylbenzyl)-3-(2-methyl-4-chlorophenyl)urea | 92.5 |
| 1-(n-Heptyl)-1-(4-n-butylbenzyl)-3-(2,4-difluorophenyl)urea | 90.0 |
| 1-(n-Heptyl)-1-(4-n-butylbenzyl)-3-(4-carboethoxyphenyl)urea | 92.4 |
| 1-(n-Heptyl)-1-(4-n-butylbenzyl)-3-(2-methylphenyl)urea | 97.4 |
| 1-(n-Heptyl)-1-(4-n-butylbenzyl)-3-(3-methylphenyl)urea | 93.8 |
| 1-(n-Heptyl)-1-(4-n-butylbenzyl)-3-(4-carboxyphenyl)urea | 61.8 |
| 1-(n-Heptyl)-1-(2-phenylethyl)-3-(2-methyl-4-chlorophenyl)urea | 93.8 |
| 1-(n-Heptyl)-1-(2-phenylethyl)-3-(2,4,5-trichlorophenyl)urea | 77.3 |
| 1-(n-Heptyl)-1-(2-phenylethyl)-3-(2-trifluoromethyl-4-chlorophenyl)urea | 88.3 |
| 1-(n-Heptyl)-1-(2-phenylethyl)-3-(2,4-dimethylphenyl)urea | 95.7 |
| 1-(n-Heptyl)-1-(2-phenylethyl)-3-(2,4-dichlorophenyl)urea | 91.8 |
| 1-(n-Heptyl)-1-(2-phenylethyl)-3-(2,4-difluorophenyl)urea | 94.1 |
| 1-(n-Heptyl)-1-(2-phenylethyl)-3-(3-trifluoromethylphenyl)urea | 88.4 |
| 1-Benzyl-1-[2-phenyl-1-(4-benzyloxyphenyl)ethyl]-3-(2,4,6-trichlorophenyl)urea | 95.0 |
| 1-(4-n-Pentylbenzyl)-1-(4-n-pentyloxybenzyl)-3-(2,4,6-trichlorophenyl)urea | 95.5 |
| 1-(4-n-Pentylbenzyl)-1-(4-n-pentyloxybenzyl)-3-(2,4 dichlorophenyl)urea | 85.0 |
| 1-(4-n-Pentylbenzyl)-1-(4-n-pentyloxybenzyl)-3-(2,4,5-trichlorophenyl)urea | 80.0 |
| 1-(4-n-Pentylbenzyl)-1-(4-n-pentyloxybenzyl)-3-(2-trifluoromethyl-4-chlorophenyl)urea | 81.0 |
| 1-(4-n-Pentylbenzyl)-1-(4-n-pentyloxybenzyl)-3-(3-trifluoromethylphenyl)urea | 85.0 |
| 1-(4-n-Pentylbenzyl)-1-(4-n-pentyloxybenzyl)-3-(2,4-difluorophenyl)urea | 90.0 |
| 1-(4-n-Pentylbenzyl)-1-(4-n-pentyloxybenzyl)-3-(2-methyl-4-chlorophenyl)urea | 91.0 |
| 1-(4-Chlorobenzyl)-1-(1-naphthylmethyl)-3-(2,4,6-trichlorophenyl)urea | 77.0 |
| 1-(4-Chlorobenzyl)-1-(1-naphthylmethyl)-3-(2-methyl-4-chlorophenyl)urea | 94.0 |
| 1-(4-Chlorobenzyl)-1-(1-naphthylmethyl)-3-(2,4-difluorophenyl)urea | 84.0 |
| 1-(4-Chlorobenzyl)-1-(1-naphthylmethyl)-3-(3-trifluoromethylphenyl)urea | 80.0 |
| 1-(4-Chlorobenzyl)-1-(1-naphthylmethyl)-3-(2,4,5-trichlorophenyl)urea | 86.0 |
| 1-Benzyl-1-[2-phenyl-1-(4-benzyloxyphenyl)ethyl]-3-(2,4,5-trichlorophenyl)urea | 95.0 |
| 1-Benzyl-1-(4-n-butyloxybenzyl)-3-(2,4,5-trichlorophenyl)urea | 89.0 |
| 1-Benzyl-1-[2-phenyl-1-(4-benzyloxyphenyl)ethyl]-3-(2,4-difluorophenyl)urea | 70.0 |
| 1-Benzyl-1-(4-n-butoxybenzyl)-3-(2,4-difluorophenyl)urea | 88.0 |
| 1-Benzyl-1-[2-phenyl-1-(4-benzyloxyphenyl)ethyl]-3-(2,4-difluorophenyl)urea | 91.0 |
| 1-Benzyl-1-[2-phenyl-1-(4-benzyloxyphenyl)ethyl]-3-(2-trifluoromethyl-4-chlorophenyl)urea | 92.0 |
| 1-Benzyl-1-[2-phenyl-1-(4-benzyloxyphenyl)ethyl]-3-(3-trifluoromethylphenyl)urea | 74.0 |
| 1-[(4-Butylphenyl)methyl]-3-(2,4-dimethylphenyl)-1-(6-hydroxyhexyl)urea | 96.8 |
| 1-[(4-Butylphenyl)methyl]-1-(6-hydroxyhexyl)-3-(2,4,5-trimethylphenyl)urea | 90.0 |
| 1-[(4-Butylphenyl)methyl]-1-[2-(2-hydroxyethoxy)ethyl]-3-(2,4,5-trimethylphenyl)urea | 85.9 |
| 1-[(4-Butylphenyl)methyl]-3-(2,4-dimethylphenyl)-1-[2-(2-hydroxyethoxy)ethyl]urea | 74.5 |
| 1-(2-Furanylmethyl)-1-heptyl-3-(2,4,5-trimethylphenyl)urea | 93.8 |
| 1-(2-Furanylmethyl)-1-heptyl-3-(2,4,6-trichlorophenyl)urea | 96.1 |
| 1-Heptyl-1-(2-thienylmethyl)-3-(2,4,5-trimethylphenyl)urea | 90.0 |
| 1-Heptyl-1-(2-thienylmethyl)-3-(2,4,6-trichlorophenyl)urea | 90.0 |
| 1-[(4-Butoxyphenyl)methyl]-1-(2-thienylmethyl)-3-(2,4,5-trimethylphenyl)urea | 90.0 |
| 1-[(4-Butylphenyl)methyl]-1-[6-[(methylsulfonyl)oxy]hexyl]-3-[(2,4,5-trimethylphenyl)methyl]urea | 90.0 |
| 1-[(4-Butylphenyl)methyl]-1-(6-cyanohexyl)-3-(2,4,5-trimethylphenyl)urea | 90.0 |
| 1-[(4-Butylphenyl)methyl]-1-(6-chlorohexyl)-3-(2,4,5-trimethylphenyl)urea | 90.0 |
| 1-[(4-Butylphenyl)methyl]-3-(4-chloro-2-methylphenyl)-1-(6-hydroxyhexyl)urea | 90.0 |
| 1-[(4-Butylphenyl)methyl]-3-(4-chloro-2-methylphenyl)-1-[6-[(methylsulfonyl)oxy]- | 90.0 |

TABLE 1-continued

| Compound | % Inhibition |
|---|---|
| hexyl]urea | |
| 1-[(4-Butylphenyl)methyl]-3-(4-chloro-2-methylphenyl)-1-(6-cyanohexyl)urea | 90.0 |
| 1-[(4-Butylphenyl)methyl]-1-(6-chlorohexyl)-3-(4-chloro-2-methylphenyl)urea | 90.0 |
| 1-[(4-Butylphenyl)methyl]-1-(6-hydroxyhexyl)-3-(2,4,6-trichlorophenyl)urea | 90.0 |
| 1-[(4-Butylphenyl)methyl]-1-[6-(methylsulfonyloxy)hexyl]-3-(2,4,6-trichlorophenyl)urea | 90.0 |
| 1-[(4-Butylphenyl)methyl]-1-(6-cyanohexyl)-3-(2,4,6-trichlorophenyl)urea | 90.0 |
| 1-[(4-Butylphenyl)methyl]-1-(6-chlorohexyl)-3-(2,4,6-trichlorophenyl)urea | 90.0 |
| 1-[(4-Butylphenyl)methyl]-3-(4-chloro-2-methylphenyl)-1-[5-(trimethylsilyl)pentyl]urea | 90.0 |
| 1-[(4-Butylphenyl)methyl]-3-(2,4-difluorophenyl)-1-[5-(trimethylsilyl)pentyl]urea | 90.0 |
| 3-(2,4-Difluorophenyl)-1-(3,3-dimethylbutyl)-1-(2-thienylmethyl)urea | 90.0 |
| 3-(4-Chloro-2-methylphenyl)-1-(3,3-dimethylbutyl)-1-(2-thienylmethyl)urea | 90.0 |
| 1-(3,3-Dimethylbutyl)-1-(2-thienylmethyl)-3-(2,4,6-trichlorophenyl)urea | 90.0 |
| 1-Benzyl-1-[2-phenyl-1-(4-benzyloxyphenyl)ethyl]-3-(2-methyl-4-chlorophenyl)urea | 89.3 |
| 1-(4-Chlorobenzyl)-1-(1-naphthylmethyl)-3-(2,4-dichlorophenyl)urea | 92.0 |
| 1-(4-Chlorobenzyl)-1-(1-naphthylmethyl)-3-(2-trifluoromethyl-4-choropnenyl)urea | 83.0 |
| 1-[2-(4-Methylphenyl)ethyl]-1-(3-chlorobenzyl)-3-(2,4-dimethylphenyl)urea | 67.6 |
| 1-[2-(4-Ethoxyphenyl)ethyl]-1-(2-chlorobenzyl)-3-(2,4-dimethylphenyl)urea | 94.1 |
| 1-(4-Phenylbenzyl)-1-(3,4-dichlorobenzyl)-3-(2,4-dimethylphenyl)urea | 36.3 |
| 1-(n-Butyl)-1-benzyl-3-(3-chloro-2-hydroxyphenyl)urea | 71.0 |
| 1-[2-(3-Fluorophenyl)ethyl]-1-(4-methylbenzyl)-3-(2,4-dimethylphenyl)urea | 80.5 |
| 1-(n-Butyl)-1-benzyl-3-(2-nitrophenyl)urea | 37.0 |
| 1-(3,4-Methylenedioxyphenyl)-1-(3,3-diphenylpropyl)-3-(2,4-dimethylphenyl)urea | 87.8 |
| 1-(n-Butyl)-1-[3-(3,4-dimethoxyphenyl)propyl]-3-(2,4-dimethylphenyl)urea | 36.4 |
| 1-(3,4-Dimethylbenzyl)-1-(2-chlorobenzyl)-3-(2,4-dimethylphenyl)urea | 92.9 |
| 1-(n-Butyl)-1-benzyl-3-(2,4,6-trichlorophenyl)urea | 87.8 |
| 1-(n-Butyl)-1-benzyl-3-(2-hydroxy-5-chlorophenyl)urea | 85.6 |
| 1-(3,4-Methylenedioxybenzyl)-1-[2-(4-methylphenyl)ethyl]-3-(2,4-dimethylphenyl)urea | 41.2 |
| 1-(n-Butyl)-1-benzyl-3-(4-amino-3,5-dichlorophenyl)urea | 61.1 |
| 1-(n-Butyl)-1-(benzyl)-3-[4-(chloroacetamido)-3,5-dichlorophenyl]urea | 72.9 |
| 1-[2-(2-Chlorophenyl)ethyl]-1-(3,4-dimethylbenzyl)-3-(2,4-dimethylphenyl)urea | 92.8 |
| 1-[2-(2-Chlorophenyl)ethyl]-1-(3-methylbenzyl)-3-(2,4-dimethylphenyl)urea | 56.1 |
| 1-(n-Butyl)-1-benzyl-3-(4-chloro-2-methylphenyl)urea | 89.0 |
| 1-(3,3-Dimethylbutyl)-1-[4-(n-butyl)benzyl]-3-(4-chloro-2-methylphenyl)urea | 90.5 |
| 1-(3,3-Dimethylbutyl)-1-[4-(n-butoxy)benzyl]-3-(4-chloro-2-methylphenyl)urea | 90.0 |
| 1-(3,3-Dimethylbutyl)-1-[4-(n-butoxy)benzyl]-3-(2,4,6-trichlorophenyl)urea | 90.0 |
| 1-(3,3-Dimethylbutyl)-1-[4-(n-butoxy)benzyl]-3-(2,4-difluorophenyl)urea | 90.0 |
| 1-(3,3-Dimethylbutyl)-1-[4-(n-butyl)benzyl]-3-(2,4-difluorophenyl)urea | 90.0 |
| 1-(3,3-Dimethylbutyl)-1-[4-(n-butyl)benzyl]-3-(2,4,6-trichlorophenyl)urea | 90.0 |
| 1-(5,5-Dimethylhexyl)-1-[4-(n-butyl)benzyl]-3-(4-chloro-2-methylphenyl)urea | 90.0 |
| 1-(5,5-Dimethylhexyl)-1-[4-(n-butyl)benzyl]-3-(2,4-difluorophenyl)urea | 90.0 |
| 1-(5,5-Dimethylhexyl)-1-[ 4-(n-butyl)benzyl]-3-(2,4,6-trichlorophenyl)urea | 90.0 |
| 1-(3,3-Dimethylbutyl)-1-(4-chlorobenzyl)-3-(4-chloro-2-methylphenyl)urea | 90.0 |
| 1-(3,3-Dimethylbutyl)-1-benzyl-3-(2,4-difluorophenyl)urea | 90.0 |
| 1-(3,3-Dimethylbutyl)-1-(4-chlorobenzyl)-3-(2,4-difluorophenyl)urea | 90.0 |
| 1-(3,3-Dimethylbutyl)-1-(4-chlorobenzyl)-3-(2,4,6-trichlorophenyl)urea | 90.0 |
| 1-(n-Heptyl)-1-[4-(n-butyl)benzyl]-3-(3-trifluoromethylphenyl)urea | 90.0 |
| 1-(3,3-Dimethylbutyl)-1-[4-(n-butyl)benzyl]-3-(3-trifluoromethylphenyl)urea | 90.0 |
| 1-(3,3-Dimethylbutyl)-1-(4-chlorobenzyl)-3-(3-trifluoromethylphenyl)urea | 90.0 |
| 1-(3,3-Dimethylbutyl)-1-[4-(2,2-dimethylpropyl)benzyl]-3-(2,4-difluorophenyl)urea | 90.0 |
| 1-(3,3-Dimethylbutyl)-1-[4-(2,2-dimethylpropyl)benzyl]-3-(4-chloro-2-methylphenyl)urea | 90.0 |
| 1-(3,3-Dimethylbutyl)-1-[4-(2,2-dimethylpropyl)benzyl]-3-(2,4,6-trichlorophenyl)urea | 90.0 |
| 1-(3,3-Dimethylbutyl)-1-[4-(n-butyl)benzyl]-3-(4-chloro-2,6-dimethylphenyl)urea | 90.0 |
| 1-(3,3-Dimethylbutyl)-1-(4-chlorobenzyl)-3-(4-chloro-2,6-dimethylphenyl)urea | 90.0 |
| 1-(n-Heptyl)-1-[4-(n-butyl)benzyl]-3-(4-chloro-2,6-dimethylphenyl)urea | 90.0 |
| 1-(3,3-Dimethylbutyl)-1-[4-(2,2-dimethylpropyl)benzyl]-3-(4-chloro-2,6-dimethylphenyl)urea | 90.0 |
| 1-(3,3-Dimethylbutyl)-1-benzyl-3-(4-chloro-2-methylphenyl)urea | 90.0 |
| 1-(n-Heptyl)-1-[4-(n-butyl)benzyl]-3-(4-chloro-2,5-dimethylphenyl)urea | 90.0 |
| 1-(3,3-Dimethylbutyl)-1-(benzyl)-3-(4-chloro-2,5-dimethylphenyl)urea | 90.0 |
| 1-(n-Heptyl)-1-[4-(n-butyl)benzyl]-3-(2,4,6-trifluorophenyl)urea | 90.0 |
| 1-(3,3-Dimethylbutyl)-1-[4-(n-butyl)benzyl]-3-(2,4,6-trifluorophenyl)urea | 90.0 |
| 1-(3,3-Dimethylbutyl)-1-[4-(2,2-dimethylpropyl)benzyl]-3-(2,4,6-trifluorophenyl)urea | 90.0 |
| 1-(3,3-Dimethylbutyl)-1-benzyl-3-(2,4,6-trifluorophenyl)urea | 90.0 |

In addition to the above described test and the results given in terms of percent inhibition, various compounds of this invention were tested by the same procedure at several concentrations. The results of this test are given in Table II in terms of IC$_{50}$ ($\mu$M), that concentration which produced 50% inhibition of the ACAT enzyme.

TABLE II

| Compound | IC$_{50}$ ($\mu$M) |
|---|---|
| 1-(6-Hydroxyheptyl)-1-[4-(2,2-dimethylpropyl)benzyl]-3-(4-chloro-2,6-dimethylphenyl)urea | 1.13 |
| 1-(Isopentyl)-1-[4-(isopropyl)benzyl]-3-(2,4-difluorophenyl)urea | 3.37 |
| 1-(Isopentyl)-1-[4-(isopropyl)benzyl]-3-(4-chloro-2,6-dimethylphenyl)urea | 0.54 |
| 1-(Isopentyl)-1-[4-(isopropyl)benzyl]-3-(2,4,6-trifluorophenyl)urea | 0.53 |
| 1-(n-Heptyl)-1-[4-(isobutyl)benzyl]-3-(4-chloro-2-methylphenyl)urea | 1.84 |
| 1-(n-Heptyl)-1-[4-(isopropyl)benzyl]-3-(2,4-difluorophenyl)urea | 1.17 |
| 1-(n-Heptyl)-1-[4-(isopropyl)benzyl]-3-(4-chloro-2,6-dimethylphenyl)urea | 0.20 |
| 1-(n-Heptyl)-1-[4-(isopropyl)benzyl]-3-(4-chloro-2-methylphenyl)urea | 1.74 |
| 1-(n-Heptyl)-1-[4-(isopropyl)benzyl]-3-(2,4,6-trifluorophenyl)urea | 0.35 |
| 1-(n-Heptyl)-1-[4-(4-isopentyl)benzyl]-3-(4- | 2.40 |

TABLE II-continued

| Compound | IC$_{50}$ ($\mu$M) |
|---|---|
| chloro-2-methylphenyl)urea | |
| 1-(n-Heptyl)-1-[4-(isopentyl)benzyl]-3-(4-chloro-2,6-dimethylphenyl)urea | 0.13 |
| 1-(n-Heptyl)-1-[4-(4-hydroxybutyl)benzyl]-3-(4-chloro-2,6-dimethylphenyl)urea | 0.82 |
| 1-(n-Heptyl)-1-[4-(3-carboxypropyl)benzyl]-3-(4-chloro-2,6-dimethylphenyl)urea | 7.22 |
| 1-(n-Heptyl)-1-[4-(4-chlorobutyl)benzyl]-3-(4-chloro-2,6-dimethylphenyl)urea | 0.11 |
| 1-(n-Heptyl)-1-[4-(3-carboethoxypropyl)benzyl]-3-(4-chloro-2,6-dimethylphenyl)urea | 1.08 |

The compounds of this invention were tested in vitro at several concentrations for their ability to inhibit the enzyme fatty acyl CoA:cholesterol acyl transferase (ACAT) using the hereinabove described procedure except that the enzyme was derived from microsomes isolated from rat intestinal mucosal cells rather than rat adrenal cells. The results of this test on representative compounds of this invention are given in Table III in terms of IC$_{50}$ ($\mu$M), that concentration which produced 50% inhibition of the ACAT enzyme.

TABLE III

| Compound | IC$_{50}$ ($\mu$M) |
|---|---|
| 1-(n-Heptyl)-1-[4-(carbomethoxymethyl)benzyl]-3-(2,4-difluorophenyl)urea | 1.75 |
| 1-(n-Heptyl)-1-[4-(carboxymethyl)benzyl]-3-(2,4-difluorophenyl)urea | 24.0 |
| 1-(n-Heptyl)-1-[4-(3-carboxypropyl)benzyl]-3-(4-chloro-2,6-dimethylphenyl)urea | 1.02 |
| 1-(n-Heptyl)-1-[4-(4-isopropylthiobutyl)benzyl]-3-(2,4-difluorophenyl)urea | 3.27 |
| 1-(n-Heptyl)-1-[4-(cyclopentylmethyl)benzyl]-3-(2,4-difluorophenyl)urea | 0.14 |
| 1-(n-Heptyl)-1-[4-(hydroxymethyl)benzyl]-3-(2,4-difluorophenyl)urea | 0.20 |
| 1-(n-Heptyl)-1-[4-(acetoxymethyl)benzyl]-3-(2,4-difluorophenyl)urea | 0.12 |
| 1-(n-Heptyl)-1-[4-(2-isopropylthioethyl)benzyl]-3-(2,4-difluorophenyl)urea | 0.21 |
| 1-(n-Heptyl)-1-[4-(2,3-dimethylpentyl)benzyl]-3-(4-chloro-2,6-dimethylphenyl)urea | 0.02 |
| 1-(n-Heptyl)-1-[4-(2-isopropylsulfinylethyl)benzyl]-3-(2,4-difluorophenyl)urea | 0.22 |
| 1-(n-Heptyl)-1-[4-(isopentyloxymethyl)benzyl]-3-(2,4-difluorophenyl)urea | 0.33 |
| 1-(n-Heptyl)-1-[4-(isopentyloxymethyl)benzyl]-3-(2,4,6-trifluorophenyl)urea | 0.18 |
| 1-(n-Heptyl)-1-[4-isopentyloxymethyl)benzyl]-3-(4-chloro-2,6-dimethylphenyl)urea | 0.13 |

Inhibition of cholesterol absorption was determined by feeding male Sprague-Dawley rats, weighing 150-170 g, a 1% cholesterol:0.5% cholic acid diet for 2 weeks. The diet also contained compounds being tested at a dose of 0.001, 0.003, 0.01, or 0.03% of the diet. Control rats were fed the same diet without any compound. At the end of the test, the rats were sacrificed by decapitation. Blood was collected, centrifuged at 1.5 times gravity for 10 minutes at 4° C.; and the serum was then analyzed for cholesterol and triglycerides enzymatically by the method of Trinder, P., Analyst, 77, 321 (1952) on a Centrifichem 400 analyzer. Livers were removed, a 0.4 g sample was taken from the center of the large lobe, and the sample was subjected to saponification using 25% saturated potassium hydroxide in ethanol. The resulting neutral sterols were extracted with petroleum ether and the extract analyzed for cholesterol. The effectiveness of the compound in inhibiting cholesterol absorption was measured by the lowering of either serum cholesterol or liver cholesterol relative the values for control rats.

Compounds which produced statistically significant inhibition of cholesterol absorption are considered to be active. Liver sterol (LS) and serum sterol (SS) values are expressed as a percentage of control values. The results of this test on typical compounds of this invention appear in Table IV.

TABLE IV

| Compound | Dose % | LS | SS |
|---|---|---|---|
| 1-Benzyl-1-(n-butyl)-3-(2,4-dimethylphenyl)urea | .03 | 65 | 70 |
| 1-Benzyl-1-(n-butyl)-3-(2,6-dimethylphenyl)urea | .03 | 91 | 68 |
| 1-Benzyl-1-(n-butyl)-3-(3,5-dimethylphenyl)urea | .03 | 75 | 93 |
| 1-Benzyl-1-(1,2-diphenylethyl)-3-(2,4-dimethylphenyl)urea | .03 | 63 | 52 |
| 1-(2-Fluorobenzyl)-1-(2-methoxybenzyl)-3-(2,4-dimethylphenyl)urea | .03 | 20 | 45 |
| 1-(n-Butyl)-1-(4-hexyloxybenzyl)-3-(2,4-trimethylphenyl)urea | .03 | 15 | 54 |
| 1-(n-Butyl)-1-(4-heptyloxybenzyl)-3-(2,4,6-trimethylphenyl)urea | .03 | 31 | 66 |
| 1-Benzyl-1-(4-n-butylbenzyl)-3-(2,4-dimethylphenyl)urea | .03 | 20 | 41 |
| 1-Benzyl-1-(4-n-butylbenzyl)-3-(2,4,6-trimethylphenyl)urea | .03 | 13 | 53 |
| 1-Benzyl-1-(4-n-butylbenzyl)-3-(4-n-butylphenyl)urea | .03 | 61 | 53 |
| 1-(n-Heptyl)-1-(4-n-butylbenzyl)-3-(2,4-dimethylphenyl)urea | .03 | 14 | 46 |
| 1-(n-Heptyl)-1-(4-n-butylbenzyl)-3-(2,4,5-trimethylphenyl)urea | .03 | 10 | 33 |
| 1-(n-Heptyl)-1-(4-butyloxybenzyl)-3-(2,4-dimethylphenyl)urea | .03 | 22 | 26 |
| 1-(n-Heptyl)-1-(4-butyloxybenzyl)-3-(2,4,5-trimethylphenyl)urea | .03 | 17 | 32 |
| 1-Benzyl-1-(4-butyloxybenzyl)-3-(2,4-dimethylphenyl)urea | .03 | 15 | 48 |
| 1-Benzyl-1-(4-butyloxybenzyl)-3-(2,4,5-trimethylphenyl)urea | .03 | 12 | 43 |
| 1-Benzyl-1-(4-n-butylbenzyl)-3-(2,4,5-trimethylphenyl)urea | .03 | 10 | 50 |
| 1-Benzyl-1-[2-phenyl-1-(4-benzyloxyphenyl)ethyl]-3-(2,4,6-trimethylphenyl)urea | .03 | 49 | 60 |
| 1-(n-Heptyl)-1-(4-n-butoxybenzyl)-3-(2,4,6-trichlorophenyl)urea | .03 | 11 | 35 |
| 1-(n-Heptyl)-(4-n-butoxybenzyl)-3-(2,4-dichlorophenyl)urea | .03 | 50 | 68 |
| 1-(n-Heptyl)-(4-n-butoxybenzyl)-3-(2-trifluoromethyl-4-chlorophenyl)urea | .03 | 35 | 59 |
| 1-Benzyl-1-(4-n-butoxybenzyl)-3-(2,4,6-trichlorophenyl)urea | .03 | 8 | 40 |
| 1-Benzyl-1-(4-n-butoxybenzyl)-3-(2,4-dichlorophenyl)urea | .03 | 49 | 53 |
| 1-Benzyl-1-(4-n-butoxybenzyl)-3-(2-trifluoromethyl-4-chlorophenyl)urea | .03 | 31 | 58 |
| 1-(n-Heptyl)-1-(4-n-butoxybenzyl)-3-(3-trifluoromethylphenyl)urea | .03 | 86 | 80 |
| 1-(n-Heptyl)-1-(4-n-butylbenzyl)-3-(2,4-dichlorophenyl)urea | .03 | 50 | 58 |
| 1-(n-Heptyl)-1-(4-n-butylbenzyl)-3-(2-trifluoromethyl-4-chlorophenyl)urea | .03 | 47 | 63 |
| 1-(n-Heptyl)-1-(4-butylbenzyl)-3-(2,4,6-trichlorophenyl)urea | .03 | 8 | 28 |
| 1-Benzyl-1-(4-n-butylbenzyl)-3-(2-methyl-4-chlorophenyl)urea | .03 | 21 | 70 |
| 1-(n-Heptyl)-1-(4-n-butoxybenzyl)-3-(2,4-difluorophenyl)urea | .03 | 25 | 63 |
| 1-(n-Heptyl)-1-(4-n-butoxybenzyl)-3-(2-methyl-4-chlorophenyl)urea | .03 | 15 | 53 |
| 1-(n-Heptyl)-1-(4-n-butylbenzyl)-3-(2-methyl-4-chlorophenyl)urea | .03 | 16 | 35 |
| 1-(n-Heptyl)-1-(4-n-butylbenzyl)-3-(2,4-difluorophenyl)urea | .03 | 19 | 35 |
| 1-(n-Heptyl)-1-(4-n-butylbenzyl)-3-(4-carboethoxyphenyl)urea | .03 | 84 | 88 |
| 1-(n-Heptyl)-1-(4-n-butylbenzyl)-3-(2- | .03 | 29 | 35 |

TABLE IV-continued

| Compound | Dose % | LS | SS |
|---|---|---|---|
| methylphenyl)urea | | | |
| 1-(n-Heptyl)-1-(4-n-butylbenzyl)-3-(3-methylphenyl)urea | .03 | 42 | 49 |
| 1-(n-Heptyl)-1-(2-phenylethyl)-3-(2-methyl-4-chlorophenyl)urea | .03 | 49 | 66 |
| 1-(n-Heptyl)-1-(2-phenylethyl)-3-(2-trifluoromethyl-4-chlorophenyl)urea | .03 | 80 | 79 |
| 1-(n-Heptyl)-1-(2-phenylethyl)-3-(2,4-dimethylphenyl)urea | .03 | 36 | 57 |
| 1-(n-Heptyl)-1-(2-phenylethyl)-3-(2,4-dichlorophenyl)urea | .03 | 88 | 81 |
| 1-(n-Heptyl)-1-(2-phenylethyl)-3-(2,4-difluorophenyl)urea | .03 | 57 | 59 |
| 1-Benzyl-1-[2-phenyl-1-(4-benzyloxyphenyl)ethyl]-3-(2,4,6-trichlorophenyl)urea | .03 | 64 | 95 |
| 1-(4-n-Pentylbenzyl)-1-(4-n-pentyloxybenzyl)-3-(2,4,6-trichlorophenyl)urea | .03 | 76 | 100 |
| 1-(4-n-Pentylbenzyl)-1-(4-n-pentyloxybenzyl)-3-(2,4-dichlorophenyl)urea | .03 | 92 | 91 |
| 1-(4-n-Pentylbenzyl)-1-(4-n-pentyloxybenzyl)-3-(2,4,5-trichlorophenyl)urea | .03 | 92 | 85 |
| 1-(4-n-Pentylbenzyl)-1-(4-n-pentyloxybenzyl)-3-(2,4-difluorophenyl)urea | .03 | 67 | 55 |
| 1-(4-Chlorobenzyl)-1-(1-naphthylmethyl)-3-(2,4,6-trichlorophenyl)urea | .03 | 12 | 38 |
| 1-(4-Chlorobenzyl)-1-(1-naphthylmethyl)-3-(2-methyl-4-chlorophenyl)urea | .03 | 17 | 35 |
| 1-(4-Chlorobenzyl)-1-(1-naphthylmethyl)-3-(2,4-difluorophenyl)urea | .03 | 30 | 45 |
| 1-(4-Chlorobenzyl)-1-(1-naphthylmethyl)-3-(3-trifluoromethylphenyl)urea | .03 | 92 | 87 |
| 1-(4-Chlorobenzyl)-1-(1-naphthylmethyl)-3-(2,4,5-trichlorophenyl)urea | .03 | 97 | 84 |
| 1-Benzyl-1-(4-n-butyloxybenzyl)-3-(2,4,5-trichlorophenyl)urea | .03 | 65 | 66 |
| 1-Benzyl-1-[2-phenyl-1-(4-benzyloxyphenyl)-ethyl]-3-(2,4-difluorophenyl)urea | .03 | 27 | 48 |
| 1-Benzyl-1-(4-n-butoxybenzyl)-3-(2,4-difluorophenyl)urea | .03 | 22 | 53 |
| 1-Benzyl-1-[2-phenyl-1-(4-benzyloxyphenyl)ethyl]-3-(2-methyl-4-chlorophenyl)urea | .03 | 31 | 50 |
| 1-(4-Chlorobenzyl)-1-(1-naphthylmethyl)-3-(2,4-dichlorophenyl)urea | .03 | 48 | 50 |
| 1-[(4-Butylphenyl)methyl]-1-(6-hydroxyhexyl)-3-(2,4,5-trimethylphenyl)urea | .03 | 39 | 57 |
| 1-[(4-Butylphenyl)methyl]-1-[2-(2-hydroxyethoxy)ethyl]-3-(2,4,5-trimethylphenyl)urea | .03 | 76 | 100 |
| 1-(2-Furanylmethyl)-1-heptyl-3-(2,4,5-trimethylphenyl)urea | .03 | 38 | 44 |
| 1-(2-Furanylmethyl)-1-heptyl-3-(2,4,6-trichlorophenyl)urea | .03 | 34 | 37 |
| 1-Heptyl-1-(2-thienylmethyl)-3-(2,4,5-trimethylphenyl)urea | .03 | 25 | 54 |
| 1-Heptyl-1-(2-thienylmethyl)-3-(2,4,6-trichlorophenyl)urea | .03 | 28 | 56 |
| 1-[(4-Butoxyphenyl)methyl]-1-(2-thienylmethyl)-3-(2,4,5-trimethylphenyl)urea | .03 | 16 | 41 |
| 1-[(4-Butylphenyl)methyl]-1-(6-cyanohexyl)-3-(2,4,5-trimethylphenyl)urea | .03 | 28 | 48 |
| 1-[(4-Butylphenyl)methyl]-1-(6-chlorohexyl)-3-(2,4,5-trimethylphenyl)urea | .03 | 15 | 40 |
| 1-[(4-Butylphenyl)methyl]-3-(4-chloro-2-methylphenyl)-1-(6-hydroxyhexyl)urea | .03 | 53 | 6 |
| 1-[(4-Butylphenyl)methyl]-3-(4-chloro-2-methylphenyl)-1-(6-cyanohexyl)urea | .03 | 50 | 48 |
| 1-[(4-Butylphenyl)methyl]-1-(6-chlorohexyl)-3-(4-chloro-2-methylphenyl)urea | .03 | 35 | 46 |
| 1-[(4-Butylphenyl)methyl]-1-(6-hydroxyhexyl)-3-(2,4,6-trichlorophenyl)urea | .03 | 32 | 35 |
| 1-[(4-Butylphenyl)methyl]-1-(6-cyanohexyl)-3-(2,4,6-trichlorophenyl)urea | .03 | 35 | 31 |
| 1-[(4-Butylphenyl)methyl]-1-(6-chlorohexyl)-3-(2,4,6-trichlorophenyl)urea | .03 | 19 | 34 |
| 1-[(4-Butylphenyl)methyl]-3-(4-chloro-2-methylphenyl)-1-[5-(trimethylsilyl)pentyl]urea | .03 | 62 | 50 |
| 1-[(4-Butylphenyl)methyl]-3-(2,4-difluorophenyl)-1-[5-(trimethylsilyl)pentyl]urea | .03 | 57 | 62 |
| 3-(2,4-Difluorophenyl)-1-(3,3-dimethylbutyl)-1-(2-thienylmethyl)urea | .03 | 73 | 66 |
| 3-(4-Chloro-2-methylphenyl)-1-(3,3-dimethylbutyl)-1-(2-thienylmethyl)urea | .03 | 64 | 62 |
| 1-(3,3-Dimethylbutyl)-1-(2-thienylmethyl)-3-(2,4,6-trichlorophenyl)urea | .03 | 56 | 58 |
| 1-[2-(4-Methylphenyl)ethyl]-1-(3-chlorobenzyl)-3-(2,4-dimethylphenyl)urea | .03 | 20 | 50 |
| 1-(4-Phenylbenzyl)-1-(3,4-dichlorobenzyl)-3-(2,4-dimethylphenyl)urea | .03 | 17 | 49 |
| 1-(3,4-Dimethylbenzyl)-1-(2-chlorobenzyl)-3-(2,4-dimethylphenyl)urea | .03 | 15 | 44 |
| 1-(n-Butyl)-1-benzyl-3-(2,4,6-trichlorophenyl)urea | .03 | 32 | 48 |
| 1-(n-Butyl)-1-benzyl-3-(4-chloro-2-methylphenyl)urea | .03 | 62 | 72 |
| 1-(3,3-Dimethylbutyl)-1-[4-(n-butyl)benzyl]-3-(4-chloro-2-methylphenyl)urea | .03 | 13 | 46 |
| 1-(3,3-Dimethylbutyl)-1-[4-(n-butoxy)benzyl]-3-(4-chloro-2-methylphenyl)urea | .03 | 22 | 61 |
| 1-(3,3-Dimethylbutyl)-1-[4-(n-butoxy)benzyl]-3-(2,4,6-trichlorophenyl)urea | .03 | 20 | 52 |
| 1-(3,3-Dimethylbutyl)-1-[4-(n-butoxy)benzyl]-3-(2,4-difluorophenyl)urea | .03 | 32 | 42 |
| 1-(3,3-Dimethylbutyl)-1-[4-(n-butyl)benzyl]-3-(2,4-difluorophenyl)urea | .03 | 30 | 39 |
| 1-(3,3-Dimethylbutyl)-1-[4-(n-butyl)benzyl]-3-(2,4,6-trichlorophenyl)urea | .03 | 13 | 37 |
| 1-(5,5-Dimethylhexyl)-1-[4-(n-butyl)benzyl]-3-(4-chloro-2-methylphenyl)urea | .03 | 34 | 42 |
| 1-(5,5-Dimethylhexyl)-1-[4-(n-butyl)benzyl]-3-(2,4-difluorophenyl)urea | .03 | 58 | 59 |
| 1-(5,5-Dimethylhexyl)-1-[4-(n-butyl)benzyl]-3-(2,4,6-trichlorophenyl)urea | .03 | 32 | 45 |
| 1-(3,3-Dimethylbutyl)-1-(4-chlorobenzyl)-3-(4-chloro-2-methylphenyl)urea | .03 | 60 | 50 |
| 1-(3,3-Dimethylbutyl)-1-benzyl-3-(2,4-difluorophenyl)urea | .03 | 70 | 71 |
| 1-(3,3-Dimethylbutyl)-1-(4-chlorobenzyl)-3-(2,4,6-trichlorophenyl)urea | .03 | 41 | 73 |
| 1-(n-Heptyl)-1-[4-(n-butyl)benzyl]-3-(4-trifluoromethylphenyl)urea | .03 | 88 | 79 |
| 1-(3,3-Dimethylbutyl)-1-[4-(n-butyl)benzyl]-3-(4-trifluoromethylphenyl)urea | .03 | 86 | 100 |
| 1-(3,3-Dimethylbutyl)-1-(4-chlorobenzyl)-3-(4-trifluoromethylphenyl)urea | .03 | 70 | 85 |
| 1-(3,3-Dimethylbutyl)-1-[4-(2,2-dimethylpropyl)benzyl]-3-(2,4-difluorophenyl)urea | .03 | 19 | 35 |
| 1-(3,3-Dimethylbutyl)-1-[4-(2,2-dimethylpropyl)benzyl]-3-(4-chloro-2-methylphenyl)urea | .03 | 20 | 51 |
| 1-(3,3-Dimethylbutyl)-1-[4-(2,2-dimethylpropyl)benzyl]-3-(2,4,6-trichlorophenyl)urea | .03 | 15 | 32 |
| 1-(3,3-Dimethylbutyl)-1-[4-(n-butyl)benzyl]-3-(4-chloro-2,6-dimethylphenyl)urea | .03 | 12 | 28 |
| 1-(3,3-Dimethylbutyl)-1-(4-chlorobenzyl)-3-(4-chloro-2,6-dimethylphenyl)urea | .03 | 25 | 46 |
| 1-(n-Heptyl)-1-[4-(n-butyl)benzyl]-3-(4-chloro-2,6-dimethylphenyl)urea | .03 | 11 | 31 |
| 1-(3,3-Dimethylbutyl)-1-[4-(2,2-dimethylpropyl)benzyl]-3-(4-chloro-2,6-dimethylphenyl)urea | .03 | 11 | 31 |
| 1-(3,3-Dimethylbutyl)-1-benzyl-3-(4-chloro-2-methylphenyl)urea | .03 | 51 | 64 |
| 1-(n-Heptyl)-1-[4-(n-butyl)benzyl]-3-(4-chloro-2,5-dimethylphenyl)urea | .03 | 19 | 48 |
| 1-(3,3-Dimethylbutyl)-1-(benzyl)-3-(4-chloro-2,5-dimethylphenyl)urea | .03 | 30 | 55 |
| 1-(Isopentyl)-1-[4-(isopropyl)benzyl]-3-(2,4-difluorophenyl)urea | .03 | 37 | 49 |
| 1-(Isopentyl)-1-[4-(isopropyl)benzyl]-3-(4-chloro-2,6-dimethylphenyl)urea | .03 | 23 | 23 |
| 1-(Isopentyl)-1-[4-(isopropyl)benzyl]-3-(2,4,6-trifluorophenyl)urea | .03 | 35 | 31 |
| 1-(n-Heptyl)-1-[4-(isobutyl)benzyl]-3-(4-chloro-2-methylphenyl)urea | .01 | 56 | 62 |
| 1-(n-Heptyl)-1-[4-(isopropyl)benzyl]-3-(2,4-difluorophenyl)urea | .01 | 64 | 77 |

TABLE IV-continued

| Compound | Dose % | LS | SS |
|---|---|---|---|
| 1-(n-Heptyl)-1-[4-(isopropyl)benzyl]-3-(4-chloro-2,6-dimethylphenyl)urea | .01 | 20 | 35 |
| 1-(n-Heptyl)-1-[4-(isopropyl)benzyl]-3-(4-chloro-2-methylphenyl)urea | .01 | 75 | 60 |
| 1-(n-Heptyl)-1-[4-(isopropyl)benzyl]-3-(2,4,6-trifluorophenyl)urea | .01 | 23 | 40 |
| 1-(n-Heptyl)-1-[4-(4-isopentyl)benzyl]-3-(4-chloro-2-methylphenyl)urea | .01 | 17 | 20 |
| 1-(n-Heptyl)-1-[4-(isopentyl)benzyl]-3-(4-chloro-2,6-dimethylphenyl)urea | .01 | 10 | 17 |
| 1-(n-Heptyl)-1-[4-(2-acetoxyethyl)benzyl]-3-(2,4-difluorophenyl)urea | .003 | 60 | 55 |
| 1-(n-Heptyl)-1-[4-(2-hydroxyethyl)benzyl]-3-(2,4-difluorophenyl)urea | .003 | 59 | 52 |
| 1-(n-Heptyl)-1-[4-(4-hydroxybutyl)benzyl]-3-(4-chloro-2,6-dimethylphenyl)urea | .01 | 26 | 24 |
| 1-(n-Heptyl)-1-[4-(4-chlorobutyl)benzyl]-3-(4-chloro-2,6-dimethylphenyl)urea | .03 | 18 | 19 |
| 1-(n-Heptyl)-1-[4-(3-carboethoxypropyl)benzyl]-3-(4-chloro-2,6-dimethylphenyl)urea | .01 | 65 | 55 |
| 1-(n-Heptyl)-1-[4-(3-methylbutoxy)benzyl]-3-(2,4-difluorophenyl)urea | .01 | 32 | 27 |
| 1-(n-Heptyl)-1-[4-(4-ethylthiobutyl)benzyl]-3-(4-chloro-2,6-dimethylphenyl)urea | .003 | 63 | 57 |
| 1-(n-Heptyl)-1-[4-(4-isopropylthiobutyl)benzyl]-3-(4-chloro-2,6-dimethylphenyl)urea | .01 | 45 | 49 |
| 1-(Isoheptyl)-1-[4-isopentyl)benzyl)-3-(2,4-difluorophenyl)urea | .003 | 45 | 24 |
| 1-(Isoheptyl)-1-[4-(isopentyl)benzyl]-3-(4-chloro-2,6-dimethylphenyl)urea | .001 | 40 | 40 |
| 1-(Isoheptyl)-1-[4-(isopentyl)benzyl]-3-(2,4,6-trifluorophenyl)urea | .001 | 45 | 33 |
| 1-(n-Heptyl)-1-[4-(2-ethylhexyl)benzyl]-3-(2,4,6-trifluorophenyl)urea | .001 | 87 | 82 |
| 1-(n-Heptyl)-1-[4-(2-ethylhexyl)benzyl]-3-(4-chloro-2,6-dimethylphenyl)urea | .001 | 87 | 83 |
| 1-(n-Heptyl)-1-[4-(2-ethylbutyl)benzyl]-3-(2,4-difluorophenyl)urea | .003 | 98 | 66 |
| 1-(n-Heptyl)-1-[4-(2-ethylbutyl)benzyl]-3-(2,4,6-trifluorophenyl)urea | .001 | 75 | 120 |
| 1-(n-Heptyl)-1-[4-(isohexyl)benzyl]-3-(2,4-difluorophenyl)urea | .003 | 53 | 45 |
| 1-(n-Heptyl)-1-[4-(isohexyl)benzyl]-3-(4-chloro-2,6-dimethylphenyl)urea | .001 | 73 | 64 |
| 1-(n-Heptyl)-1-[4-(isohexyl)benzyl]-3-(2,4,6-trifluorophenyl)urea | .001 | 78 | 77 |
| 1-(n-Heptyl)-1-[4-(cyclopentyl)benzyl]-3-(2,4-difluorophenyl)urea | .003 | 82 | 80 |
| 1-(n-Heptyl)-1-[4-(cyclopentyl)benzyl]-3-(4-chloro-2,6-dichlorophenyl)urea | .003 | 36 | 35 |
| 1-(n-Heptyl)-1-[4-(2-ethylhexyl)benzyl]-3-(2,4-difluorophenyl)urea | .003 | 56 | 63 |
| 1-(n-Heptyl)-1-[4-(cyclopentyl)benzyl]-3-(2,4,6-trifluorophenyl)urea | .001 | 58 | 69 |
| 1-(n-Heptyl)-1-[4-(2-ethylbutyl)benzyl]-3-(4-chloro-2,6-dimethylphenyl)urea | .001 | 94 | 62 |
| 1-(n-Heptyl)-1-[4-(2-methylpentyl)benzyl]-3-(2,4-difluorophenyl)urea | .003 | 72 | 53 |
| 1-(n-Heptyl)-1-[4-(2-methylpentyl)benzyl]-3-(2,4,6-trifluorophenyl)urea | .001 | 75 | 93 |
| 1-(n-Heptyl)-1-[4-(2-methylpentyl)benzyl]-3-(4-chloro-2,6-dimethylphenyl)urea | .001 | 56 | 61 |
| 1-(n-Heptyl)-1-[4-(3-methylpentyl)benzyl]-3-(2,4-difluorophenyl)urea | .001 | 89 | 72 |
| 1-(n-Heptyl)-1-[4-(3-methylpentyl)benzyl]-3-(2,4,6-trifluorophenyl)urea | .003 | 46 | 36 |
| 1-(n-Heptyl)-1-[4-(3-methylpentyl)benzyl]-3-(4-chloro-2,6-dimethylphenyl)urea | .003 | 45 | 38 |
| 1-(n-Heptyl)-1-[4-(cyclobutylmethyl)benzyl]-3-(4-chloro-2,6-dimethylphenyl)urea | .001 | 69 | 64 |
| 1-(n-Heptyl)-1-[4-(cyclopentylmethyl)benzyl]-3-(2,4,6-trifluorophenyl)urea | .003 | 50 | 62 |
| 1-(n-Heptyl)-1-[4-(cyclopentylmethyl)benzyl]-3-(2,4-difluorophenyl)urea | .01 | 80 | — |
| 1-(n-Heptyl)-1-[4-(cyclobutylmethyl)benzyl]-3-(2,4,6-trifluorophenyl)urea | .001 | 66 | 62 |
| 1-(n-Heptyl)-1-[4-(1,5-dimethylhexyl)benzyl]-3-(2,4-difluorophenyl)urea | .001 | 88 | 83 |
| 1-(n-Heptyl)-1-[4-(1,5-dimethylhexyl)benzyl]-3-(4-chloro-2,6-dimethylphenyl)urea | .001 | 100 | 94 |
| 1-(n-Heptyl)-1-[4-(1,5-dimethylhexyl)benzyl]-3-(2,4,6-trifluoromethylphenyl)urea | .003 | 65 | 57 |
| 1-(n-Heptyl)-1-[4-(cyclopentylmethyl)benzyl]-3-(4-chloro-2,6-dimethylphenyl)urea | .003 | 53 | 45 |
| 1-(n-Heptyl)-1-[4-(hydroxymethyl)benzyl]-3-(2,4-difluorophenyl)urea | .003 | 81 | — |
| 1-(n-Heptyl)-1-[4-(acetoxymethyl)benzyl]-3-(2,4-difluorophenyl)urea | .01 | 70 | — |
| 1-(n-Heptyl)-1-[4-(isopentyloxy)benzyl]-3-(4-chloro-2,6-dimethylphenyl)urea | .001 | 23 | 25 |
| 1-(n-Heptyl)-1-[4-(isopentyloxy)benzyl]-3-(2,4-difluorophenyl)urea | .001 | 61 | 69 |
| 1-(n-Heptyl)-1-[4-(2-methylbutyl)benzyl]-3-(2,4-difluorophenyl)urea | .01 | 42 | 36 |
| 1-(n-Heptyl)-1-[4-(2-methylbutyl)benzyl]-3-(2,4,6-trifluorophenyl)urea | .001 | 64 | 76 |
| 1-(n-Heptyl)-1-[4-(2-isopropylthioethyl)benzyl]-3-(4-chloro-2,6-dimethylphenyl)urea | .003 | 51 | 49 |
| 1-(n-Heptyl)-1-[4-(2-isopropylsulfonylethyl)benzyl]-3-(2,4-difluorophenyl)urea | .003 | 68 | 94 |
| 1-(n-Heptyl)-1-[4-(2-isopropylsulfonylethyl)benzyl]-3-(4-chloro-2,6-dimethylphenyl)urea | .003 | 54 | 57 |
| 1-(n-Heptyl)-1-[4-(2,3-dimethylpentyl)benzyl]-3-(2,4-difluorophenyl)urea | .01 | 63 | 48 |
| 1-(n-Heptyl)-1-[4-(2-isopropylthioethyl)benzyl]-3-(2,4-difluorophenyl)urea | .003 | 72 | — |
| 1-(n-Heptyl)-1-[4-(2-isopropylsulfinylethyl)benzyl]-3-(4-chloro-2,6-dimethylphenyl)urea | .003 | 54 | 45 |
| 1-(n-Heptyl)-1-[4-(2,3-dimethylpentyl)benzyl]-3-(2,4,6-trifluorophenyl)urea | .01 | 31 | 33 |
| 1-(n-Heptyl)-1-[4-(2,2-dimethylpropyl)benzyl]-3-(2,4-difluorophenyl)urea | .01 | 51 | 22 |
| 1-(n-Heptyl)-1-[4-(2,2-dimethylpropyl)benzyl]-3-(2,4,6-trifluorophenyl)urea | .003 | 55 | 38 |
| 1-(n-Heptyl)-1-[4-(2,2-dimethylpropyl)benzyl]-3-(4-chloro-2,6-dimethylphenyl)urea | .003 | 54 | 41 |
| 1-(n-Heptyl)-1-[4-(2,3-dimethylpentyl)benzyl]-3-(4-chloro-2,6-dimethylphenyl)urea | .01 | 40 | 43 |
| 1-(n-Heptyl)-1-[4-(2-isopropylsulfinylethyl)benzyl]-3-(2,4-difluorophenyl)urea | .003 | 84 | — |
| 1-(n-Heptyl)-1-[4-(isopentyloxymethyl)benzyl]-3-(2,4-difluorophenyl)urea | .01 | 60 | — |
| 1-(n-Heptyl)-1-[4-(isopentyloxymethyl)benzyl]-3-(2,4,6-trifluorophenyl)urea | .001 | 75 | — |
| 1-(n-Heptyl)-1-[4-(isopentyloxymethyl)benzyl]-3-(4-chloro-2,6-dimethylphenyl)urea | .003 | 47 | — |

The tests reported or shown in Table I, II, III and IV, inclusive, have been actually carried out and the results therein actually obtained or concluded therefrom.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing, for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed may vary depending on the particular compound employed, the mode of administration, and the severity of the condition being treated. In general, however, satisfactory results are obtained when the compounds of the invention are administered at a daily dosage of from about 2 mg to about 500 mg/kg of animal body weight, preferably given in divided doses two to four times a day, or in sustained release form. For most large mammals, the total daily dosage is from about 100 mg to about 5,000 mg, preferably from about 100 mg to 2,000 mg. Dosage forms suitable for internal use comprise from about 25 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared as glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent of dispersion medium containing, for example, water, ethanol, polyol (e.g., glycerol, propylene glycol, and liquid polyethylene glycol), suitable mixtures thereof, and vegetable oils.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

1-Benzyl-1-(n-butyl)-3-(2,4-dimethylphenyl)urea

A solution of 4.89 g of 2,4-dimethylphenylisocyanate in 100 ml of hexane is added to a solution of 4.41 g of N-benzyl-n-butylamine in 150 ml of hexane, and the solution is stirred at room temperature for 2 hours and then evaporated. The residual solid is recrystallized from pentane to yield 1-benzyl-1-(n-butyl)-3-(2,4-dimethylphenyl)urea, m.p. 70°–71° C.

With reference to Example 1 and Table V, only those examples with listed characteristics have been actually carried out. All other examples are simulated or predicted.

TABLE V

| Example | Compound | M.P. °C. |
|---|---|---|
| 2 | 1-Benzyl-1-(n-butyl)-3-(2-methylphenyl)urea | 48–53 |
| 3 | 1-Benzyl-1-(n-butyl)-3-(3-methylphenyl)urea | 91–92 |
| 4 | 1-Benzyl-1-(n-butyl)-3-(4-methylphenyl)urea | 102–103 |
| 5 | 1-Benzyl-1-(n-butyl)-3-(3-ethylphenyl)urea | |
| 6 | 1-Benzyl-1-(n-butyl)-3-(4-ethylphenyl)urea | |
| 7 | 1-Benzyl-1-(n-butyl)-3-(4-isopropylphenyl)urea | |
| 8 | 1-Benzyl-1-(n-butyl)-3-(4-n-butylphenyl)urea | |
| 9 | 1-Benzyl-1-(n-butyl)-3-(2,3-dimethylphenyl)urea | 77–78 |
| 10 | 1-Benzyl-1-(n-butyl)-3-(2,5-dimethylphenyl)urea | 87–89 |
| 11 | 1-Benzyl-1-(n-butyl)-3-(2,6-dimethylphenyl)urea | 125–126 |
| 12 | 1-Benzyl-1-(n-butyl)-3-(3,4-dimethylphenyl)urea | 94–95 |
| 13 | 1-Benzyl-1-(n-butyl)-3-(3,5-dimethylphenyl)urea | 108–109 |
| 14 | 1-Benzyl-1-(n-butyl)-3-(2,4,5-trimethylphenyl)urea | |
| 15 | 1-Benzyl-1-(n-butyl)-3-(2,4,6-trimethylphenyl)urea | 141–144 |
| 16 | 1-Benzyl-1-(n-butyl)-3-(4-methoxyphenyl)urea | |
| 17 | 1-Benzyl-1-(n-butyl)-3-(4-n-butoxyphenyl)urea | |
| 18 | 1-Benzyl-1-(n-butyl)-3-(3,4,5-trimethoxyphenyl)urea | 144–145 |
| 19 | 1-Benzyl-1-(n-butyl)-3-(4-methylthiophenyl)urea | |
| 20 | 1-Benzyl-1-(n-butyl)-3-(2-chlorophenyl)urea | – |
| 21 | 1-Benzyl-1-(n-butyl)-3-(4-chlorophenyl)urea | |
| 22 | 1-Benzyl-1-(n-butyl)-3-(2-bromophenyl)urea | |
| 23 | 1-Benzyl-1-(n-butyl)-3-(4-bromophenyl)urea | |
| 24 | 1-Benzyl-1-(n-butyl)-3-(4-fluorophenyl)urea | |
| 25 | 1-Benzyl-1-(n-butyl)-3-(4-iodophenyl)urea | |
| 26 | 1-Benzyl-1-(n-butyl)-3-(2,3-dichlorophenyl)urea | |
| 27 | 1-Benzyl-1-(n-butyl)-3-(2,4-dichlorophenyl)urea | |

TABLE V-continued

| Example | Compound | M.P. °C. |
|---|---|---|
| 28 | 1-Benzyl-1-(n-butyl)-3-(2,5-dichlorophenyl)urea | |
| 29 | 1-Benzyl-1-(n-butyl)-3-(3,4-dichlorophenyl)urea | 102–105 |
| 30 | 1-Benzyl-1-(n-butyl)-3-(3,5-dichlorophenyl)urea | 100–103 |
| 31 | 1-Benzyl-1-(n-butyl)-3-(2,4,6-trichlorophenyl)urea | 94–96 |
| 32 | 1-Benzyl-1-(n-butyl)-3-(2,4-difluorophenyl)urea | |
| 33 | 1-Benzyl-1-(n-butyl)-3-(3-trifluoromethylphenyl)urea | 86–87 |
| 34 | 1-Benzyl-1-(n-butyl)-3-(3-acetylphenyl)urea | |
| 35 | 1-Benzyl-1-(n-butyl)-3-(4-acetylphenyl)urea | |
| 36 | 1-Benzyl-1-(n-butyl)-3-(4-carboethoxyphenyl)urea | |
| 37 | 1-Benzyl-1-(n-butyl)-3-(4-phenoxyphenyl)urea | |
| 38 | 1-Benzyl-1-(n-butyl)-3-(2-cyanophenyl)urea | |
| 39 | 1-Benzyl-1-(n-butyl)-3-(3-chloro-2-methoxyphenyl)urea | 52–54 |
| 40 | 1-Benzyl-1-(n-butyl)-3-(5-chloro-4-methoxyphenyl)urea | 61–63 |
| 41 | 1-Benzyl-1-(n-butyl)-3-(2,6-dibromo-4-fluorophenyl)urea | |
| 42 | 1-Benzyl-1-(n-butyl)-3-(2-nitro-4-methylphenyl)urea | |
| 43 | 1-Benzyl-1-(n-butyl)-3-(3-chloro-4-methylphenyl)urea | yellow oil |
| 44 | 1-Benzyl-1-(n-butyl)-3-(4-chloro-3-trifluoromethylphenyl)urea | |
| 45 | 1-Benzyl-1-(n-butyl)-3-(4-chloro-3-trifluoromethylphenyl)urea | |
| 46 | 1-Benzyl-1-(n-butyl)-3-(2-chloro-5-trifluoromethylphenyl)urea | |
| 47 | 1-Benzyl-1-(n-butyl)-3-(3,4-methylenedioxyphenyl)urea | |
| 48 | 1-Benzyl-1-(n-butyl)-3-(4-phenylphenyl)urea | |
| 49 | 1-Benzyl-1-(n-butyl)-3-(4-benzylphenyl)urea | |
| 50 | 1-Benzyl-1-(sec-butyl)-3-(2,4-dimethylphenyl)urea | |
| 51 | 1-Benzyl-1-(tert-butyl)-3-(4-methylphenyl)urea | |
| 52 | 1-Benzyl-1-(n-hexyl)-3-(4-ethylphenyl)urea | |
| 53 | 1-Benzyl-1-(n-heptyl)-3-(2-methylphenyl)urea | |
| 54 | 1-Benzyl-1-(n-octyl)-3-(2-methylphenyl)urea | |
| 55 | 1-Benzyl-1-(n-nonyl)-3-(4-carboethoxyphenyl)urea | |
| 56 | 1-Benzyl-1-(n-undecyl)-3-(2-methylphenyl)urea | |
| 57 | 1-Benzyl-1-(n-tridecyl)-3-(methylphenyl)urea | |
| 58 | 1-Benzyl-1-(n-tetradecyl)-3-(2-methylphenyl)urea | |
| 59 | 1-Benzyl-1-(n-hexadecyl)-3-(2-methylphenyl)urea | |
| 60 | 1-Benzyl-1-(n-octadecyl)-3-(3-chlorophenyl)urea | |
| 61 | 1-(2-Phenylethyl)-1-(sec-butyl)-3-(2,4-dimethylphenyl)urea | |
| 62 | 1-(2-Phenylethyl)-1-(n-hexyl)-3-(3-chloro-4-methylphenyl)urea | |
| 63 | 1-(2-Phenylethyl)-1-(n-heptyl)-3-(4-chlorophenyl)urea | |
| 64 | 1-(2-Phenylethyl)-1-(n-octyl)-3-(4-carboethoxyphenyl)urea | |
| 65 | 1-(2-Phenylethyl)-1-(n-nonyl)-3-(2,4-dimethylphenyl)urea | |
| 66 | 1-(2-Phenylethyl)-1-(n-decyl)-3-(2,4-dichlorophenyl)urea | |
| 67 | 1-(2-Phenylethyl)-1-(n-undecyl)-3-(3-methylphenyl)urea | |
| 68 | 1-(2-Phenylethyl)-1-(n-tridecyl)-3-(2-chlorophenyl)urea | |
| 69 | 1-(2-Phenylethyl)-1-(n-hexadecyl)-3-(4-methylphenyl)urea | |
| 70 | 1-(4-Phenyl-n-butyl)-1-(n-hexyl)-3-(3-methylphenyl)urea | |
| 71 | 1-(4-Phenyl-n-butyl)-1-(n-heptyl)-3-(2,4-dimethylphenyl)urea | |
| 72 | 1-(4-Phenyl-n-butyl)-1-(n-octyl)-3-(4-methylphenyl)urea | |
| 73 | 1-(4-Phenyl-n-butyl)-1-(n-nonyl)-3-(2,4-dichlorophenyl)urea | |
| 74 | 1-(4-Phenyl-n-butyl)-1-(n-decyl)-3-(3-chloro-4-methylphenyl)urea | |
| 75 | 1-(4-Phenyl-n-butyl)-1-(n-undecyl)-3-(4-chlorophenyl)urea | |
| 76 | 1-(4-Phenyl-n-butyl)-1-(n-dodecyl)-3-(3-chlorophenyl)urea | |
| 77 | 1-(4-Phenyl-n-butyl)-1-(n-tetradecyl)-3-(3-methylphenyl)urea | |
| 78 | 1-(4-Phenyl-n-butyl)-1-(n-octadecyl)-3-(2,4-dimethylphenyl)urea | |
| 79 | 1-Benzyl-1-(1,2-diphenylethyl)-3-(2,4-dimethylphenyl)urea | 157–158 |
| 80 | 1-Benzyl-1-[1-(3-methoxyphenyl)-2-phenylethyl]-3-(2,4-dimethylphenyl)urea | 124–126 |
| 81 | 1-Benzyl-1-[1-(4-benzyloxyphenyl)-2-phenyl]-3-(2,4-dimethylphenyl)urea | 140–141 |
| 82 | N—(2,4-dimethylphenyl)-3,4-dihydro-1-(phenylmethyl)-2(1H)-isoquinolinecarboxamide | |
| 83 | 1-Benzyl-1-[1-(3-methoxyphenyl)-2-phenylethyl]-3-(3-trifluoromethylphenyl)urea | 125–126 |
| 84 | 1-Benzyl-1-(2-phenylethyl)-3-(2,4-dimethylphenyl)urea | |
| 85 | 1-Benzyl-1-(4-phenyl-n-butyl)-3-(2,4-dimethylphenyl)urea | |
| 86 | 1-Benzyl-1-(n-pentyl)-3-(2,4-dimethylphenyl)urea | oil |
| 87 | 1-Benzyl-1-(n-hexyl)-3-(2,4-dimethylphenyl)urea | oil |
| 88 | 1-Benzyl-1-(n-octyl)-3-(2,4-dimethylphenyl)urea | oil |
| 89 | 1-Benzyl-1-(n-undecyl)-3-(2,4-dimethylphenyl)urea | oil |
| 90 | 1-Benzyl-1-(4-cyclohexyl-n-butyl)-3-(2,4-dimethylphenyl)urea | |
| 91 | 1-Benzyl-1-(cyclopentyl)-3-(2,4-dimethylphenyl)urea | |
| 92 | 1-Benzyl-1-(1-naphthylmethyl)-3-(2,4-dimethylphenyl)urea | |
| 93 | 1-Benzyl-1-(3-chlorobenzyl)-3-(2,4-dimethylphenyl)urea | |
| 94 | 1-Benzyl-1-(4-chlorobenzyl)-3-(2,4-dimethylphenyl)urea | |
| 95 | 1-Benzyl-1-[2-(4-chlorophenyl)ethyl]-3-(2,4-dimethylphenyl)urea | |
| 96 | 1-Benzyl-1-(2,4-dichlorobenzyl)-3-(2,4-dimethylphenyl)urea | |
| 97 | 1-Benzyl-1-(4-methoxybenzyl)-3-(2,4-dimethylphenyl)urea | |
| 98 | 1-Benzyl-1-[2-(2-methoxyphenyl)ethyl]-3-(2,4-dimethylphenyl)urea | |
| 99 | 1-Benzyl-1-(4-methylbenzyl)-3-(2,4-dimethylphenyl)urea | |
| 100 | 1-Benzyl-1-(3-methylbenzyl)-3-(2,4-dimethylphenyl)urea | |
| 101 | 1-Benzyl-1-[2-(4-methylphenyl)ethyl]-3-(2,4-dimethylphenyl)urea | |
| 102 | 1-Benzyl-1-(2-phenylethyl)-3-(3-chloro-4-methylphenyl)urea | |
| 103 | 1-Benzyl-1-(4-phenyl-n-butyl)-3-(3-chloro-4-methylphenyl)urea | |
| 104 | 1-Benzyl-1-(n-heptyl)-3-(3-chloro-4-methylphenyl)urea | |

TABLE V-continued

| Example | Compound | M.P. °C. |
|---|---|---|
| 105 | 1-Benzyl-1-(n-octyl)-3-(3-chloro-4-methylphenyl)urea | |
| 106 | 1-Benzyl-1-(n-decyl)-3-(3-chloro-4-methylphenyl)urea | |
| 107 | 1-Benzyl-1-(n-undecyl)-3-(3-chloro-4-methylphenyl)urea | |
| 108 | 1-Benzyl-1-(n-tridecyl)-3-(3-chloro-4-methylphenyl)urea | |
| 109 | 1-Benzyl-1-(n-tetradecyl)-3-(3-chloro-4-methylphenyl)urea | |
| 110 | 1-Benzyl-1-(n-hexadecyl)-3-(3-chloro-4-methylphenyl)urea | |
| 111 | 1-Benzyl-1-(n-octadecyl)-3-(3-chloro-4-methylphenyl)urea | |
| 112 | 1-Benzyl-1-(cyclohexyl)-3-(3-chloro-4-methylphenyl)urea | |
| 113 | 1-Benzyl-1-(1-naphthylmethyl)-3-(3-chloro-4-methylphenyl)urea | |
| 114 | 1-Benzyl-1-(4-chlorobenzyl)-3-(3-chloro-4-methylphenyl)urea | |
| 115 | 1-Benzyl-1-(4-methylbenzyl)-3-(3-chloro-4-methylphenyl)urea | |
| 116 | 1-Benzyl-1-(n-hexyl)-3-(4-methylphenyl)urea | |
| 117 | 1-Benzyl-1-(n-octyl)-3-(4-methylphenyl)urea | |
| 118 | 1-Benzyl-1-(n-undecyl)-3-(4-methylphenyl)urea | |
| 119 | 1-Benzyl-1-(n-tetradecyl)-3-(4-methylphenyl)urea | |
| 120 | 1-Benzyl-1-(n-hexadecyl)-3-(4-methylphenyl)urea | |
| 121 | 1-Benzyl-1-(n-octadecyl)-3-(4-methylphenyl)urea | |
| 122 | 1-Benzyl-1-(1-naphthylmethyl)-3-(4-methylphenyl)urea | |
| 123 | 1-Benzyl-1-(cyclopentyl)-3-(4-methylphenyl)urea | |
| 124 | 1-Benzyl-1-(4-chlorobenzyl)-3-(4-methylphenyl)urea | |
| 125 | 1-Benzyl-1-(4-methylbenzyl)-3-(4-methylphenyl)urea | |
| 126 | 1-Benzyl-1-(n-pentyl)-3-(4-chlorophenyl)urea | |
| 127 | 1-Benzyl-1-(n-heptyl)-3-(4-chlorophenyl)urea | |
| 128 | 1-Benzyl-1-(n-nonyl)-3-(4-chlorophenyl)urea | |
| 129 | 1-Benzyl-1-(n-decyl)-3-(4-chlorophenyl)urea | |
| 130 | 1-Benzyl-1-(n-tridecyl)-3-(4-chlorophenyl)urea | |
| 131 | 1-Benzyl-1-(n-tetradecyl)-3-(4-chlorophenyl)urea | |
| 132 | 1-Benzyl-1-(n-hexadecyl)-3-(4-chlorophenyl)urea | |
| 133 | 1-Benzyl-1-(1-naphthylmethyl)-3-(4-chlorophenyl)urea | |
| 134 | 1-Benzyl-1-(cyclohexyl)-3-(4-chlorophenyl)urea | |
| 135 | 1-Benzyl-1-(cyclopentyl)-3-(4-chlorophenyl)urea | |
| 136 | 1-Benzyl-1-(4-chlorobenzyl)-3-(4-chlorophenyl)urea | |
| 137 | 1-Benzyl-1-(3-chlorobenzyl)-3-(4-chlorophenyl)urea | |
| 138 | 1-Benzyl-1-(4-methylbenzyl)-3-(4-chlorophenyl)urea | |
| 139 | 1-Benzyl-1-(n-hexyl)-3-(3,4-dichlorophenyl)urea | |
| 140 | 1-Benzyl-1-(n-octyl)-3-(3,4-dichlorophenyl)urea | |
| 141 | 1-Benzyl-1-(n-undecyl)-3-(3,4-dichlorophenyl)urea | |
| 142 | 1-Benzyl-1-(n-tetradecyl)-3-(3,4-dichlorophenyl)urea | |
| 143 | 1-Benzyl-1-(n-octadecyl)-3-(3,4-dichlorophenyl)urea | |
| 144 | 1-Benzyl-1-(cyclohexyl)-3-(3,4-dichlorophenyl)urea | |
| 145 | 1-Benzyl-1-(1-naphthylmethyl)-3-(3,4-dichlorophenyl)urea | |
| 146 | 1-Benzyl-1-(3-chlorobenzyl)-3-(3,4-dichlorophenyl)urea | |
| 147 | 1-Benzyl-1-(4-chlorobenzyl)-3-(3,4-dichlorophenyl)urea | |
| 148 | 1-Benzyl-1-(3-methylbenzyl)-3-(3,4-dichlorophenyl)urea | |
| 149 | 1-Benzyl-1-(4-methylbenzyl)-3-(3,4-dichlorophenyl)urea | |
| 150 | 1-Benzyl-1-(n-butyl)-3-(3-phenyl)thiourea | 83–85 |
| 151 | 1-Benzyl-1-(n-butyl)-3-(2-methylphenyl)thiourea | |
| 152 | 1-Benzyl-1-(n-butyl)-3-(3-methylphenyl)thiourea | |
| 153 | 1-Benzyl-1-(n-butyl)-3-(4-methylphenyl)thiourea | |
| 154 | 1-Benzyl-1-(n-butyl)-3-(3-ethylphenyl)thiourea | |
| 155 | 1-Benzyl-1-(n-butyl)-3-(4-ethylphenyl)theourea | |
| 156 | 1-Benzyl-1-(n-butyl)-3-(4-isopropylphenyl)thiourea | |
| 157 | 1-Benzyl-1-(n-butyl)-3-(4-n-butylphenyl)thiourea | |
| 158 | 1-Benzyl-1-(n-butyl)-3-(2,3-dimethylphenyl)thiourea | |
| 159 | 1-Benzyl-1-(n-butyl)-3-(2,5-dimethylphenyl)thiourea | |
| 160 | 1-Benzyl-1-(n-butyl)-3-(2,6-dimethylphenyl)thiourea | |
| 161 | 1-Benzyl-1-(n-butyl)-3-(3,4-dimethylphenyl)thiourea | |
| 162 | 1-Benzyl-1-(n-butyl)-3-(3,5-dimethylphenyl)thiourea | |
| 163 | 1-Benzyl-1-(n-butyl)-3-(2,4,5-trimethylphenyl)thiourea | |
| 164 | 1-Benzyl-1-(n-butyl)-3-(2,4,6-trimethylphenyl)thiourea | |
| 165 | 1-Benzyl-1-(n-butyl)-3-(4-methoxyphenyl)thiourea | |
| 166 | 1-Benzyl-1-(n-butyl)-3-(2,4-dimethoxyphenyl)thiourea | |
| 167 | 1-Benzyl-1-(n-butyl)-3-(3-methylthiophenyl)thiourea | |
| 168 | 1-Benzyl-1-(n-butyl)-3-(2-chlorophenyl)thiourea | |
| 169 | 1-Benzyl-1-(n-butyl)-3-(3-chlorophenyl)thiourea | |
| 170 | 1-Benzyl-1-(n-butyl)-3-(4-chlorophenyl)thiourea | |
| 171 | 1-Benzyl-1-(n-butyl)-3-(2-bromophenyl)thiourea | |
| 172 | 1-Benzyl-1-(n-butyl)-3-(4-bromophenyl)thiourea | |
| 173 | 1-Benzyl-1-(n-butyl)-3-(4-fluorophenyl)thiourea | |
| 174 | 1-Benzyl-1-(n-butyl))-3-(4-iodophenyl)thiourea | |
| 175 | 1-Benzyl-1-(n-butyl)-3-(2,3-dichlorophenyl)thiourea | |
| 176 | 1-Benzyl-1-(n-butyl)-3-(2,4-dichlorophenyl)thiourea | |
| 177 | 1-Benzyl-1-(n-butyl)-3-(2,5-dichlorophenyl)thiourea | |
| 178 | 1-Benzyl-1-(n-butyl)-3-(3,5-dichlorophenyl)thiourea | |
| 179 | 1-Benzyl-1-(n-butyl)-3-(2,4,6-trichlorophenyl)thiourea | |
| 180 | 1-Benzyl-1-(n-butyl)-3-(2,4-difluorophenyl)thiourea | |
| 181 | 1-Benzyl-1-(4-phenyl-n-butyl)-3-(2,4-dimethylphenyl)thiourea | |
| 182 | 1-Benzyl-1-(n-hexyl)-3-(2,4-dimethylphenyl)thiourea | |
| 183 | 1-Benzyl-1-(n-undecyl)-3-(2,4-dimethylphenyl)thiourea | |
| 184 | 1-Benzyl-1-(n-tetradecyl)-3-(2,4-dimethylphenyl)thiourea | |
| 185 | 1-Benzyl-1-(n-hexadecyl)-3-(2,4-dimethylphenyl)thiourea | |

TABLE V-continued

| Example | Compound | M.P. °C. |
|---|---|---|
| 186 | 1-Benzyl-1-(4-cyclohexyl-n-butyl)-3-(2,4-dimethylphenyl)thiourea | |
| 187 | 1-Benzyl-1-(cyclopentyl)-3-(2,4-dimethylphenyl)thiourea | |
| 188 | 1-Benzyl-1-(1-naphthylmethyl)-3-(2,4-dimethylphenyl)thiourea | |
| 189 | 1-Benzyl-1-(3-chlorobenzyl)-3-(2,4-dimethylphenyl)thiourea | |
| 190 | 1-Benzyl-1-(4-chlorobenzyl)-3-(2,4-dimethylphenyl)thiourea | |
| 191 | 1-Benzyl-1-[2-(4-chlorophenyl)ethyl]-3-(2,4-dimethylphenyl)thiourea | |
| 192 | 1-Benzyl-1-(2,4-dichlorobenzyl)-3-(2,4-dimethylphenyl)thiourea | |
| 193 | 1-Benzyl-1-(4-methoxybenzyl)-3-(2,4-dimethylphenyl)thiourea | |
| 194 | 1-Benzyl-1-[2-(2-methoxyphenyl)ethyl]-3-(2,4-dimethylphenyl)thiourea | |
| 195 | 1-Benzyl-1-(4-methylbenzyl)-3-(2,4-dimethylphenyl)thiourea | |
| 196 | 1-Benzyl-1-(3-methylbenzyl)-3-(2,4-dimethylphenyl)thiourea | |
| 197 | 1-Benzyl-1-[2-(4-methylphenyl)ethyl]-3-(2,4-dimethylphenyl)thiourea | |
| 198 | 1-Benzyl-1-(2-phenylethyl)-3-(3-chloro-4-methylphenyl)thiourea | |
| 199 | 1-Benzyl-1-(4-phenyl-n-butyl)-3-(3-chloro-4-methylphenyl)thiourea | |
| 200 | 1-Benzyl-1-(n-heptyl)-3-(3-chloro-4-methylphenyl)thiourea | |
| 201 | 1-Benzyl-1-(n-octyl)-3-(3-chloro-4-methylphenyl)thiourea | |
| 202 | 1-Benzyl-1-(n-butyl)-3-(3-chloro-2-methoxyphenyl)urea | 52–54 |
| 203 | 1-Benzyl-1-(n-butyl)-3-(5-chloro-2-methoxyphenyl)urea | 161–163 |
| 204 | 1-(n-Butyl)-1-(2-fluorobenzyl)-3-(2,4-dimethylphenyl)urea | 76–77 |
| 205 | 1-(n-Butyl)-1-(4-fluorobenzyl)-3-(2,4-dimethylphenyl)urea | 78–79 |
| 206 | 1-(n-Butyl)-1-(2-chlorobenzyl)-3-(2,4-dimethylphenyl)urea | 101–102 |
| 207 | 1-(n-Butyl)-1-(2,6-dichlorobenzyl)-3-(2,4-dimethylphenyl)urea | 145–146 |
| 208 | 1-(4-Bromobenzyl)-1-(n-butyl)-3-(2,4-dimethylphenyl)urea | 61–63 |
| 209 | 1-(n-Butyl)-1-(4-n-butylbenzyl)-3-(2,4-dimethylphenyl)urea | 60–62 |
| 210 | 1-(n-Butyl)-1-(4-methylbenzyl)-3-(2,4-dimethylphenyl)urea | oil |
| 211 | 1-(n-Butyl)-1-(4-tert-butylbenzyl)-3-(2,4-dimethylphenyl)urea | 28–31 |
| 212 | 1-(n-Butyl)-1-(4-chlorobenzyl)-3-(2,4-dimethylphenyl)urea | oil |
| 213 | 1-(n-Butyl)-1-(4-methoxybenzyl)-3-(2,4-dimethylphenyl)urea | oil |
| 214 | 1-(n-Butyl)-1-(3,4-methylenedioxybenzyl)-3-(2,4-dimethylphenyl)urea | oil |
| 215 | 1-(n-Butyl)-1-(4-trifluoromethylbenzyl)-3-(2,4-dimethylphenyl)urea | oil |
| 216 | 1-(n-Butyl)-1-(4-phenylbenzyl)-3-(2,4-dimethylphenyl)urea | 82–83 |
| 217 | 1-(n-Butyl)-1-(2-phenylethyl)-3-(2,4-dimethylphenyl)urea | oil |
| 218 | 1-(n-Butyl)-1-[2-(4-fluorophenyl)ethyl]-3-(2,4-dimethylphenyl)urea | oil |
| 219 | 1-(n-Butyl)-1-[2-(4-chlorophenyl)ethyl]-3-(2,4-dimethylphenyl)urea | oil |
| 220 | 1-(n-Butyl)-1-[2-(3-methoxyphenyl)ethyl]-3-(2,4-dimethylphenyl)urea | oil |
| 221 | 1-(n-Butyl)-1-(3-phenylpropyl)-3-(2,4-dimethylphenyl)urea | oil |
| 222 | 1-(n-Butyl)-1-[4-(n-pentyl)benzyl]-3-(2,4-dimethylphenyl)urea | 65–67 |
| 223 | 1-(n-Butyl)-1-[4-(n-hexyl)benzyl]-3-(2,4-dimethylphenyl)urea | oil |
| 224 | 1-(n-Butyl)-1-(3-chlorobenzyl)-3-(2,4-dimethylphenyl)urea | oil |
| 225 | 1-(n-Butyl)-1-[4-(n-butoxy)benzyl]-3-(2,4-dimethylphenyl)urea | oil |
| 226 | 1-(n-Butyl)-1-[4-(n-pentyloxy)benzyl]-3-(2,4-dimethylphenyl)urea | oil |
| 227 | 1-(n-Butyl)-1-[4-(n-hexyloxy)benzyl]-3-(2,4-dimethylphenyl)urea | oil |
| 228 | 1-(n-Butyl)-1-[4-(n-heptyloxy)benzyl]-3-(2,4-dimethylphenyl)urea | oil |
| 229 | 1-(n-Butyl)-1-(4-nitrobenzyl)-3-(2,4-dimethylphenyl)urea | oil |
| 230 | 1-(n-Butyl)-1-[2-(2-methylphenyl)ethyl]-3-(2,4-dimethylphenyl)urea | 102–103 |
| 231 | 1-(n-Butyl)-1-[2-(3-methylphenyl)ethyl]-3-(2,4-dimethylphenyl)urea | oil |
| 232 | 1-(n-Butyl)-1-[2-(4-methylphenyl)ethyl]-3-(2,4-dimethylphenyl)urea | oil |
| 233 | 1-(n-Butyl)-1-[2-(4-ethoxyphenyl)ethyl]-3-(2,4-dimethylphenyl)urea | oil |
| 234 | 1-(n-Butyl)-1-[2-(3-fluorophenyl)ethyl]-3-(2,4-dimethylphenyl)urea | oil |
| 235 | 1-(n-Butyl)-1-[2-(2-chlorophenyl)ethyl]-3-(2,4-dimethylphenyl)urea | oil |
| 236 | 1-(n-Butyl)-1-[2-(3-chlorophenyl)ethyl]-3-(2,4-dimethylphenyl)urea | oil |
| 237 | 1-(n-Butyl)-1-[2-(4-bromophenyl)ethyl]-3-(2,4-dimethylphenyl)urea | oil |
| 238 | 1-(n-Butyl)-1-[2-(3,4-dimethoxyphenyl)ethyl-3-(2,4-dimethylphenyl)urea | oil |
| 239 | 1-(n-Butyl)-1-(2-adamantylethyl)-3-(2,4-dimethylphenyl)urea | 134–135 |
| 240 | 1-(n-Butyl)-1-(3-cyclohexyl-2-phenylethyl)-3-(2,4-dimethylphenyl)urea | 112–113 |
| 241 | 1-(n-Butyl)-1-(di-(4-chlorophenyl)ethyl)-3-(2,4-dimethylphenyl)urea | 145–147 |
| 242 | 1-(n-Butyl)-1-(2,4-dichlorobenzyl)-3-(2,4-dimethylphenyl)urea | 120–121 |
| 243 | 1-(n-Butyl)-1-(3-trifluoromethylbenzyl)-1-(4-fluorobenzyl)-3-(2,4-dimethylphenyl)urea | 114–115 |
| 244 | 1-(4-Chlorobenzyl)-1-(1-naphthylmethyl-3-(2,4-dimethylphenyl)urea | 134–136 |
| 245 | 1-(4-Methoxybenzyl)-1-(2,4-dichlorobenzyl)-3-(2,4-dimethylphenyl)urea | 124 126 |
| 246 | 1-(3-Chlorobenzyl)-1-(4-methoxybenzyl)-3-(2,4-dimethylphenyl)urea | 108–109 |
| 247 | 1-(4-Phenylbenzyl)-1-(3,4-dichlorobenzyl)-3-(2,4-dimethylphenyl)urea | 103–105 |
| 248 | 1-(2-Fluorobenzyl)-1-(4-methylbenzyl)-3-(2,4-dimethylphenyl)urea | 128–130 |
| 249 | 1-(4-Chlorobenzyl)-1(3,4-dimethoxybenzyl)-3-(2,4-dimethylphenyl)urea | 94–96 |
| 250 | 1-(4-Fluorobenzyl)-1-(3,4-methylenedioxybenzyl)-3-(2,4-dimethylphenyl)urea | 122–124 |
| 251 | 1-(n-Butyl)-1-(4-methylthiobenzyl)-3-(2,4-dimethylphenyl)urea | oil |
| 252 | 1-(2,4-Dichlorobenzyl)-1-(4-methylthiobenzyl)-3-(2,4-dimethylphenyl)urea | 124–125 |
| 253 | 1-[2-(3,4-Dimethoxyphenyl)ethyl]-1-(3,4-methylenedioxybenzyl)-3-(2,4-dimethylphenyl)urea | oil |
| 254 | 1-[2-(2-Methylphenyl)ethyl]-1-(2,4-dichlorobenzyl)-3-(2,4-dimethylphenyl)urea | 120–122 |
| 255 | 1-[2-(4-Methylphenyl)ethyl]-1-(4-chlorobenzyl)-3-(2,4-dimethylphenyl)urea | oil |
| 256 | 1-[2-(4-Ethoxyphenyl)ethyl]-1-(2-chlorobenzyl)-3-(2,4-dimethylphenyl)urea | oil |
| 257 | 1-[2-(3-Fluorophenyl)ethyl]-1-(3-methoxybenzyl)-3-(2,4-dimethylphenyl)urea | 94–95 |

TABLE V-continued

| Example | Compound | M.P. °C. |
|---|---|---|
| 258 | 1-[2-(3-Methoxyphenyl)ethyl]-1-(3-chlorobenzyl)-3-(2,4-dimethylphenyl)urea | 73–74 |
| 259 | 1-(3,3-Diphenylpropyl)-1-(4-fluorobenzyl)-3-(2,4-dimethylphenyl)urea | 109–110 |
| 260 | 1-(n-Butyl)-1-(3,3-diphenylpropyl)-3-(2,4-dimethylphenyl)urea | 94–95 |
| 261 | 1-(n-Butyl)-1-(4-cyclohexylbutyl)-3-(2,4-dimethylphenyl)urea | oil |
| 262 | 1-[2-(3,4-Dimethoxyphenyl)ethyl]-1-(3-chloro-4-methylbenzyl)-3-(2,4-dimethylphenyl)urea | gum |
| 263 | 1-[2-(2-Methylphenyl)ethyl]-1-(4-bromobenzyl)-3-(2,4-dimethylphenyl)urea | 126–127 |
| 264 | 1-[2-(3-Trifluoromethylphenyl)ethyl]-1-(2-chlorobenzyl)-3-(2,4-dimethylphenyl)urea | 115–117 |
| 265 | 1-(2-Fluorobenzyl)-1-(2-methoxybenzyl)-3-(2,4-dimethylphenyl)urea | 96–98 |
| 266 | 1-[2-(3,4-Dimethoxyphenyl)ethyl]-1-(4-fluorobenzyl)-3-(2,4-dimethylphenyl)urea | gum |
| 267 | 1-[2-(4-Ethoxyphenyl)ethyl]-1-(2,4-dimethylbenzyl)-3-(2,4-dimethylphenyl)urea | gum |
| 268 | 1-[2-(3-Methylphenyl)ethyl]-1-(3-nitrobenzyl)-3-(2,4-dimethylphenyl)urea | 99–101 |
| 269 | 1-[2-(2,5-Dimethoxyphenyl)ethyl]-1-(3-chlorobenzyl)-3-(2,4-dimethylphenyl)urea | 86–88 |
| 270 | 1-(n-Butyl)-1-(2-methyl-2,2-diphenyl)ethyl-3-(2,4-dimethylphenyl)urea | 159–160 |
| 271 | 1-(n-Butyl)-1-(4-hexyloxybenzyl)-3-(2,4,6-trimethylphenyl)urea | 90–91 |
| 272 | 1-(n-Butyl)-1-(4-heptyloxybenzyl)-3-(2,4,6-trimethylphenyl)urea | 86–87 |
| 273 | 1-(n-Butyl)-1-benzyl-3-(4-trifluoroacetylamino-3,5-dichlorophenyl)urea | 173–175 |
| 274 | 1-Benzyl-1-(4-n-butylbenzyl)-3-(2,4-dimethylphenyl)urea | oil |
| 275 | 1-Benzyl-1-(4-n-butylbenzyl)-3-(2,4,6-trimethylphenyl)urea | oil |
| 276 | 1-Benzyl-1-(4-n-butylbenzyl)-3-(4-n-butylphenyl)urea | yellow oil |
| 277 | 1-Benzyl-1-(4-n-butylbenzyl)-3-(4-phenoxyphenyl)urea | 79–80 |
| 278 | 1-(n-Heptyl)-1-(4-n-butylbenzyl)-3-(2,4-dimethylphenyl)urea | yellow oil |
| 279 | 1-(n-Heptyl)-1-(4-n-butylbenzyl)-3-(2,4,5-trimethylphenyl)urea | yellow oil |
| 280 | 1-Benzyl-1-[2-phenyl-1-(4-benzyloxyphenyl)ethyl]-3-(2,4,5-trimethylphenyl)urea | 157–158 |
| 281 | 1-(n-Heptyl)-1-(4-butyloxybenzyl)-3-(2,4-dimethylphenyl)urea | oil |
| 282 | 1-(n-Heptyl)-1-(4-butyloxybenzyl)-3-(2,4,5-trimethylphenyl)urea | yellow oil |
| 283 | 1-Benzyl-1-(4-butyloxybenzyl)-3-(2,4-dimethylphenyl)urea | solid |
| 284 | 1-Benzyl-1-(4-butyloxybenzyl)-3-(2,4,5-trimethlphenyl)urea | solid |
| 285 | 1-Benzyl-1-(4-n-butylbenzyl)-3-(2,4,5-trimethylphenyl)urea | yellow oil |
| 286 | 1-Benzyl-1-[2-phenyl-1-(4-benzyloxyphenyl)ethyl]-3-(2,4,6-trimethylphenyl)urea | 140–141 |
| 287 | 1-(n-Heptyl)-1-(4-n-butoxybenzyl)-3-(2,4,6-trichlorophenyl)urea | 63–64 |
| 288 | 1-(n-Heptyl)-(4-n-butoxybenzyl)-3-(2,4-dichlorophenyl)urea | gum |
| 289 | 1-(n-Heptyl)-(4-n-butoxybenzyl)-3-(2-trifluoromethyl-4-chlorophenyl)urea | gum |
| 290 | 1-Benzyl-1-(4-n-butoxybenzyl)-3-(2,4,6-trichlorophenyl)urea | 91–93 |
| 291 | 1-Benzyl-1-(4-n-butoxybenzyl)-3-(2,4-dichlorophenyl)urea | gum |
| 292 | 1-Benzyl-1-(4-n-butoxybenzyl)-3-(2-trifluoromethyl-4-chlorophenyl)urea | gum |
| 293 | 1-(n-Heptyl)-1-(4-n-butoxybenzyl)-3-(3-trifluoromethylphenyl)urea | gum |
| 294 | 1-(n-Benzyl)-1-(4-n-butoxybenzyl)-3-(3-trifluoromethylphenyl)urea | gum |
| 295 | 1-(n-Heptyl)-1-(4-n-butylbenzyl)-3-(2,4-dichlorophenyl)urea | gum |
| 296 | 1-(n-Heptyl)-1-(4-n-butylbenzyl)-3-(2-trifluoromethyl-4-chlorophenyl)urea | gum |
| 297 | 1-(n-Heptyl)-1-(4-n-butylbenzyl)-3-(2,4,6-trichlorophenyl)urea | gum |
| 298 | 1-(n-Heptyl)-1-(4-n-butylbenzyl)-3-(3-trifluoromethylphenyl)urea | gum |
| 299 | 1-(n-Heptyl)-1-(4-n-butylbenzyl)-3-(2,4,5-trichlorophenyl)urea | gum |
| 300 | 1-Benzyl-1-(4-n-butoxybenzyl)-3-(2-methyl-4-chlorophenyl)urea | 107–108 |
| 301 | 1-(n-Heptyl)-1-(4-n-butoxybenzyl)-3-(2,4-difluorophenyl)urea | gum |
| 302 | 1-(n-Heptyl)-1-(4-n-butoxybenzyl)-3-(2-methyl-4-chlorophenyl)urea | gum |
| 303 | 1-(n-Heptyl)-1-(2-furyl)-3-(2,4,5-trimethylphenyl)urea | 65–67 |
| 304 | 1-(n-Heptyl)-1-(2-furyl)-3-(2,4,6-trichlorophenyl)urea | yellow oil |
| 305 | 1-(n-Heptyl)-1-(4-n-butylbenzyl)-3-(2-methyl-4-chlorophenyl)urea | oil |
| 306 | 1-(n-Heptyl)-1-(4-n-butylbenzyl)-3-(4-carboethoxyphenyl)urea | 65–66 |
| 307 | 1-(n-Heptyl)-1-(4-n-butylbenzyl)-3-(2-methylphenyl)urea | oil |
| 308 | 1-(n-Heptyl)-1-(4-n-butylbenzyl)-3-(3-methylphenyl)urea | oil |
| 309 | 1-(n-Heptyl)-1-(4-n-butylbenzyl)-3-(4-carboxyphenyl)urea | 147–149 |
| 310 | 1-(n-Heptyl)-1-(2-phenylethyl)-3-(2-methyl-4-chlorophenyl)urea | gum |
| 311 | 1-(n-Heptyl)-1-(2-phenylethyl)-3-(2,4,5-trichlorophenyl)urea | gum |
| 312 | 1-(n-Heptyl)-1-(2-phenylethyl)-3-(2-trifluoromethyl-4-chlorophenyl)urea | gum |
| 313 | 1-(n-Heptyl)-1-(2-phenylethyl)-3-(2,4-dimethylphenyl)urea | gum |
| 314 | 1-(n-Heptyl)-1-(2-phenylethyl)-3-(2,4-dichlorophenyl)urea | gum |
| 315 | 1-(n-Heptyl)-1-(2-phenylethyl)-3-(2,4-difluorophenyl)urea | gum |
| 316 | 1-(n-Heptyl)-1-(2-phenylethyl)-3-(3-trifluoromethylphenyl)urea | gum |
| 317 | 1-Benzyl-1-[2-phenyl-1-(4-benzyloxyphenyl)ethyl]-3-(2,4,6-trichlorophenyl)urea | 131–133 |
| 318 | 1-(4-n-Pentylbenzyl)-1-(4-n-pentyloxybenzyl)-3-(2,4,6-trichlorophenyl)urea | oil |
| 319 | 1-(4-n-Pentylbenzyl)-1-(4-n-pentyloxybenzyl)-3-(2,4-dichlorophenyl)urea | oil |
| 320 | 1-(4-n-Pentylbenzyl)-1-(4-n-pentyloxybenzyl)-3-(2,4,5-trichloro- | oil |

TABLE V-continued

| Example | Compound | M.P. °C. |
|---|---|---|
| | phenyl)urea | |
| 321 | 1-(4-n-Pentylbenzyl)-1-(4-n-pentyloxybenzyl)-3-(2-trifluoromethyl-4-chlorophenyl)urea | oil |
| 322 | 1-(4-n-Pentylbenzyl)-1-(4-n-pentyloxybenzyl)-3-(3-trifluoromethylphenyl)urea | oil |
| 323 | 1-(4-n-Pentylbenzyl)-1-(4-n-pentyloxybenzyl)-3-(2,4-difluorophenyl)urea | oil |
| 324 | 1-(4-n-Pentylbenzyl)-1-(4-n-pentyloxybenzyl)-3-(2-methyl-4-chlorophenyl)urea | oil |
| 325 | 1-(4-Chlorobenzyl)-1-(1-naphthylmethyl)-3-(2,4,6-trichlorophenyl)urea | 157–159 |
| 326 | 1-(4-Chlorobenzyl)-1-(1-naphthylmethyl)-3-(2-methyl-4-chlorophenyl)urea | 168–169 |
| 327 | 1-(4-Chlorobenzyl)-1-(1-naphthylmethyl)-3-(2,4-difluorophenyl)urea | 122–124 |
| 328 | 1-(4-Chlorobenzyl)-1-(1-naphthylmethyl)-3-(3-trifluoromethylphenyl)urea | 127–129 |
| 329 | 1-(4-Chlorobenzyl)-1-(1-naphthylmethyl)-3-(2,4,5-trichlorophenyl)urea | 110–113 |
| 330 | 1-Benzyl-1-[2-phenyl-1-(4-benzyloxyphenyl)ethyl]-3-(2,4,5-trichlorophenyl)urea | 142–145 |
| 331 | 1-Benzyl-1-(4-n-butyloxybenzyl)-3-(2,4,5-trichlorophenyl)urea | oil |
| 332 | 1-Benzyl-1-[2-phenyl-1-(4-benzyloxyphenyl)ethyl]-3-(2,4-difluorophenyl)urea | 84–85 |
| 333 | 1-Benzyl-1-(4-n-butoxybenzyl)-3-(2,4-difluorophenyl)urea | oil |
| 334 | 1-Benzyl-1-[2-phenyl-1-(4-benzyloxyphenyl)ethyl]-3-(2,4-dichlorophenyl)urea | 126–128 |
| 335 | 1-Benzyl-1-[2-phenyl-1-(4-benzyloxyphenyl)ethyl]-3-(2-trifluoromethyl-4-chlorophenyl)urea | 99–101 |
| 336 | 1-Benzyl-1-[2-phenyl-1-(4-benzyloxyphenyl)ethyl]-3-(3-trifluoromethylphenyl)urea | 102–104 |
| 337 | 1-Benzyl-1-[2-phenyl-1-(4-benzyloxyphenyl)ethyl]-3-(2-methyl-4-chlorophenyl)urea | 125–126 |
| 338 | 1-(4-Chlorobenzyl)-1-(1-naphthylmethyl)-3-(2,4-dichlorophenyl)urea | 96–98 |
| 339 | 1-(4-Chlorobenzyl)-1-(1-naphthylmethyl)-3-(2-trifluoromethyl-4-chlorophenyl)urea | yellow glass |
| 340 | 1-[2-(4-Methylphenyl)ethyl]-1-(3-chlorobenzyl)-3-(2,4-dimethylphenyl)urea | 34–35 |
| 341 | 1-(n-Butyl)-1-benzyl-3-(3-chloro-2-hydroxyphenyl)urea | 59–62 |
| 342 | 1-[2-(3-Fluorophenyl)ethyl]-1-(4-methylbenzyl)-3-(2,4-dimethylphenyl)urea | 74–75 |
| 343 | 1-(n-Butyl)-1-benzyl-3-(2-nitrophenyl)urea | yellow oil |
| 344 | 1-(3,4-Methylenedioxyphenyl)-1-(3,3-diphenylpropyl)-3-(2,4-dimethylphenyl)urea | 135–137 |
| 345 | 1-(n-Butyl)-1-[3-(3,4-dimethoxyphenyl)propyl]-3-(2,4-dimethylphenyl)urea | yellow oil |
| 346 | 1-(3,4-Dimethylbenzyl)-1-(2-chlorobenzyl)-3-(2,4-dimethylphenyl)urea | 113–115 |
| 347 | 1-(n-Butyl)-1-benzyl-3-(2-hydroxy-5-chlorophenyl)urea | 113–115 |
| 348 | 1-(3,4-Dimethoxybenzyl)-1-[2-(4-methylphenyl)ethyl]-3-(2,4-dimethylphenyl)urea | gum |
| 349 | 1-(n-Butyl)-1-benzyl-3-(4-amino-3,5-dichlorophenyl)urea | 121–124 |
| 350 | 1-(n-Butyl)-1-(benzyl)-3-[4-(chloroacetamido)-3,5-dichlorophenyl]urea | 135–138 |
| 351 | 1-[2-(2-Chlorophenyl)ethyl]-1-(3,4-dimethylbenzyl)-3-(2,4-dimethylphenyl)urea | 96–98 |
| 352 | 1-[2-(2-Chlorophenyl)ethyl]-1-(3-methylbenzyl)-3-(2,4-dimethylphenyl)urea | 92–95 |
| 353 | 1-(n-Butyl)-1-benzyl-3-(4-chloro-2-methylphenyl)urea | 83–84 |
| 354 | 1-(3,3-Dimethylbutyl)-1-[4-(n-butyl)benzyl]-3-(4-chloro-2-methylphenyl)urea | 88–91 |
| 355 | 1-(3,3-Dimethylbutyl)-1-[4-(n-butoxy)benzyl]-3-(4-chloro-2-methylphenyl)urea | 106–107 |
| 356 | 1-(3,3-Dimethylbutyl)-1-[4-(n-butoxy)benzyl]-3-(2,4,6-trichlorophenyl)urea | 114–115 |
| 357 | 1-(3,3-Dimethylbutyl)-1-[4-(n-butoxy)benzyl]-3-(2,4-difluorophenyl)urea | oil |
| 358 | 1-(3,3-Dimethylbutyl)-1-[4-(n-butyl)benzyl]-3-(2,4-difluorophenyl)urea | oil |
| 359 | 1-(3,3-Dimethylbutyl)-1-[4-(n-butyl)benzyl]-3-(2,4,6-trichlorophenyl)urea | solid |
| 360 | 1-(5,5-Dimethylhexyl)-1-[4-(n-butyl)benzyl]-3-(4-chloro-2-methylphenyl)urea | oil |
| 361 | 1-(5,5-Dimethylhexyl)-1-[4-(n-butyl)benzyl]-3-(2,4-difluorophenyl)urea | oil |
| 362 | 1-(5,5-Dimethylhexyl)-1-[4-(n-butyl)benzyl]-3-(2,4,6-trichlorophenyl)urea | oil |
| 363 | 1-(3,3-Dimethylbutyl)-1-(4-chlorobenzyl)-3-(4-chloro-2-methylphenyl)urea | 110–111 |
| 364 | 1-(3,3-Dimethylbutyl)-1-benzyl-3-(2,4-difluorophenyl)urea | 82–84 |
| 365 | 1-(3,3-Dimethylbutyl)-1-(4-chlorobenzyl)-3-(2,4-difluorophenyl)urea | 67–70 |
| 366 | 1-(3,3-Dimethylbutyl)-1-(4-chlorobenzyl)-3-(2,4,6-trichlorophenyl)urea | 148–149 |
| 367 | 1-(n-Heptyl)-1-[4-(n-butyl)benzyl]-3-(4-trifluoromethylphenyl)urea | 69–71 |

TABLE V-continued

| Example | Compound | M.P. °C. |
|---|---|---|
| 368 | 1-(3,3-Dimethylbutyl)-1-[4-butyl)benzyl]-3-(4-trifluoromethylphenyl)urea | 103–104 |
| 369 | 1-(3,3-Dimethylbutyl)-1-(4-chlorobenzyl)-3-(4-trifluoromethylphenyl)urea | 140–141 |
| 370 | 1-(3,3-Dimethylbutyl)-1-[4-(2,2-dimethylpropyl)benzyl]-3-(2,4-difluorophenyl)urea | oil |
| 371 | 1-(3,3-Dimethylbutyl)-1-[4-(2,2-dimethylpropyl)benzyl]-3-(4-chloro-2-methylphenyl)urea | 125–130 |
| 372 | 1-(3,3-Dimethylbutyl)-1-[4-(2,2-dimethylpropyl)benzyl]-3-(2,4,6-trichlorophenyl)urea | glass |
| 373 | 1-(3,3-Dimethylbutyl)-1-[4-(n-butyl)benzyl]-3-(4-chloro-2,6-dimethylphenyl)urea | 138–139 |
| 374 | 1-(3,3-Dimethylbutyl)-1-(4-chlorobenzyl)-3-(4-chloro-2,6-dimethylphenyl)urea | 178–180 |
| 375 | 1-(n-Heptyl)-1-[4-(n-butyl)benzyl]-3-(4-chloro-2,6-dimethylphenyl)urea | 48–50 |
| 376 | 1-(3,3-Dimethylbutyl)-1-[4-(2,2-dimethylpropyl)benzyl]-3-(4-chloro-2,6-dimethylphenyl)urea | 148–150 |
| 377 | 1-(3,3-Dimethylbutyl)-1-benzyl-3-(4-chloro-2-methylphenyl)urea | 114–115 |
| 378 | 1-(n-Heptyl)-1-[4-(n-butyl)benzyl]-3-(4-chloro-2,5-dimethylphenyl)urea | oil |
| 379 | 1-(3,3-Dimethylbutyl)-1-(benzyl)-3-(4-chloro-2,5-dimethylphenyl)urea | solid |
| 380 | 1-(3,3-Dimethylbutyl)-1-[4-(n-butyl)benzyl]-3-(4-chloro-2,5-dimethylphenyl)urea | 102–103 |
| 381 | 1-(3,3-Dimethylbutyl)-1-[4-(2,2-dimethylpropyl)benzyl]-3-(4-chloro-2,5-dimethylphenyl)urea | 160–161 |
| 382 | 1-[(4-butylphenyl)methyl]-1-[3,3-dimethylbutyl]-3-[2,4,6-trifluorophenyl]urea | oil |
| 383 | 1-[(4-butylphenyl)methyl]-1-(n-heptyl)-3-[2,4,6-trifluorophenyl]urea | 35–36 |
| 384 | 1-[(4-butoxyphenyl)methyl]-1-[3,3-dimethylbutyl]-3-[2,4,6-trifluorophenyl]urea | |
| 385 | 1-[(4-butoxyphenyl)methyl]-1-(n-heptyl)-3-[2,4,6-trifluorophenyl]urea | |
| 386 | 1-Benzyl-1-[3,3-dimethylbutyl]-3-[2,4,6-trifluorophenyl]urea | 108–110 |
| 387 | 1-Benzyl-1-(n-heptyl)-3-[2,4,6-trifluorophenyl]urea | |
| 388 | 1-[3,3-dimethylbutyl]-1-[[4-(2,2-dimethylpropyl)phenyl]methyl]-3-[2,4,6-trifluorophenyl]urea | 39–40 |
| 389 | 1-[(4-chlorophenyl)methyl]-1-[3,3-dimethylbutyl]-3-[2,4,6-trifluorophenyl]urea | |
| 390 | 1-(n-Heptyl)-1-[4-(2,2-dimethylpropyl)phenylmethyl]-3-(2,4-difluorophenyl)urea | 40–46 |
| 391 | 1-(n-Heptyl)-1-[4-(2,2-dimethylpropyl)phenylmethyl]-3-(4-chloro-2,6-dimethylphenyl)urea | 111–113 |
| 392 | 1-(n-Heptyl)-1-[4-(2,2-dimethylpropyl)phenylmethyl]-3-(2,4,6-trifluorophenyl)urea | oil |
| 393 | 1-(n-Heptyl)-1-(4-isobutylphenylmethyl)-3-(2,4-difluorophenyl)urea | |
| 394 | 1-(n-Heptyl)-1-(4-isobutylphenylmethyl)-3-(4-chloro-2,6-dimethylphenyl)urea | 87–88 |
| 395 | 1-(n-Heptyl)-1-(4-isobutylphenylmethyl)-3-(2,4,6-trifluorophenyl)urea | 73–74 |
| 396 | 1-(n-Heptyl)-1-(4-isopentylphenylmethyl)-3-(2,4-difluorophenyl)urea | oil |
| 397 | 1-(n-Heptyl)-1-(4-isopentylphenylmethyl)-3-(4-chloro-2,6-dimethylphenyl)urea | oil |
| 398 | 1-(n-Heptyl)-1-(4-isopentylphenylmethyl)-3-(2,4,6-trifluorophenyl)urea | oil |
| 399 | 1-(6-Hydroxyheptyl)-1-[4-(2,2-dimethylpropyl)benzyl]-3-(4-chloro-2,6-dimethylpyhenyl)urea | oil |
| 400 | 1-(Isopentyl)-1-[4-(isopropyl)benzyl]-3-(2,4-difluorophenyl)urea | oil |
| 401 | 1-(Isopentyl)-1-[4-(isopropyl)benzyl]-3-(4-chloro-2,6-dimethylphenyl)urea | 115–117 |
| 402 | 1-(Isopentyl)-1-[4-(isopropyl)benzyl]-3-(2,4,6-trifluorophenyl)urea | oil |
| 403 | 1-(6-Hydroxyheptyl)-1-[4-(2,2-dimethylpropyl)benzyl]-3-(2,4-difluorophenyl)urea | oil |
| 404 | 1-(n-Heptyl)-1-[4-(isobutyl)benzyl]-3-(4-chloro-2-methylphenyl)urea | oil |
| 405 | 1-(n-Heptyl)-1-[4-(isopropyl)benzyl]-3-(2,4-difluorophenyl)urea | oil |
| 406 | 1-(n-Heptyl)-1-[ 4-(isopropyl)benzyl]-3-(4-chloro-2,6-dimethylphenyl)urea | 121–123 |
| 407 | 1-(n-Heptyl)-1-[4-(isopropyl)benzyl]-3-(4-chloro-2-methylphenyl)urea | oil |
| 408 | 1-(n-Heptyl)-1-[4-(isopropyl)benzyl]-3-(2,4,6-trifluorophenyl)urea | 60–61 |
| 409 | 1-(n-Heptyl)-1-[4-(4-isopentyl)benzyl]-3-(4-chloro-2-methylphenyl)urea | oil |
| 410 | 1-(n-Heptyl)-1-[4-(isopentyl)benzyl]-3-(4-chloro-2,6-dimethylphenyl)urea | 48–52 |
| 411 | 1-(n-Heptyl)-1-[4-(2-acetoxyethyl)benzyl]-3-(2,4-difluorophenyl)urea | oil |
| 412 | 1-(n-Heptyl)-1-[4-(2-hydroxyethyl)benzyl]-3-(2,4-difluorophenyl)urea | oil |
| 413 | 1-(n-Heptyl)-1-[4-carbomethoxymethyl)benzyl]-3-(2,4-difluorophenyl)urea | oil |
| 414 | 1-(n-Heptyl)-1-[4-(carboxymethyl)benzyl]-3-(2,4-difluorophenyl)urea | solid |
| 415 | 1-(n-Heptyl)-1-[4-(4-hydroxybutyl)benzyl]-3-(4-chloro-2,6-dimethylphenyl)urea | 65–66 |
| 416 | 1-(n-Heptyl)-1-[4-(3-carboxypropyl)benzyl]-3-(4-chloro-2,6-dimethylphenyl)urea | oil |
| 417 | 1-(n-Heptyl)-1-[4-(4-chlorobutyl)benzyl]-3-(4-chloro-2,6-dimethyl- | oil |

TABLE V-continued

| Example | Compound | M.P. °C. |
|---|---|---|
| | phenyl)urea | |
| 418 | 1-(n-Heptyl)-1-[4-(3-carboethoxypropyl)benzyl]-3-(4-chloro-2,6-dimethylphenyl)urea | oil |
| 419 | 1-(n-Heptyl)-1-[4-(3-methylbutoxy)benzyl]-3-(2,4-difluorophenyl)urea | oil |
| 420 | 1-(n-Heptyl)-1-[4-(4-ethylthiobutyl)benzyl]-3-(4-chloro-2,6-dimethylphenyl)urea | 47–52 |
| 421 | 1-(n-Heptyl)-1-[4-(4-isopropylthiobutyl)benzyl]-3-(4-chloro-2,6-dimethylphenyl)urea | 40–44 |
| 422 | 1-(Isoheptyl)-1-[4-(isopentyl)benzyl]-3-(2,4-difluorophenyl)urea | oil |
| 423 | 1-(Isoheptyl)-1-[4-(isopentyl)benzyl]-3-(4-chloro-2,6-dimethylphenyl)urea | 84–86 |
| 424 | 1-(Isoheptyl)-1-[4-(isopentyl)benzyl]-3-(2,4,6-trifluorophenyl)urea | oil |
| 425 | 1-(n-Heptyl)-1-[4-(4-isopropylthiobutyl)benzyl]-3-(2,4-difluorophenyl)urea | oil |
| 426 | 1-(n-Heptyl)-1-[4-(isohexyloxy)benzyl]-3-(2,4-difluorophenyl)urea | oil |
| 427 | 1-(n-Heptyl)-1-[4-(2-ethylhexyl)benzyl]-3-(2,4,6-trifluorophenyl)urea | oil |
| 428 | 1-(n-Heptyl)-1-[4-(2-ethylhexyl)benzyl]-3-(4-chloro-2,6-dimethylphenyl)urea | oil |
| 429 | 1-(n-Heptyl)-1-[4-(2-ethylbutyl)benzyl]-3-(2,4-difluorophenyl)urea | oil |
| 430 | 1-(n-Heptyl)-1-[4-(2-ethylbutyl)benzyl]-3-(2,4,6-trifluorophenyl)urea | oil |
| 431 | 1-(n-Heptyl)-1-[4-(isohexyl)benzyl]-3-(2,4-difluorophenyl)urea | oil |
| 432 | 1-(n-Heptyl)-1-[4-(isohexyl)benzyl]-3-(4-chloro-2,6-dimethylphenyl)urea | 56–61 |
| 433 | 1-(n-Heptyl)-1-[4-(isohexyl)benzyl]-3-(2,4,6-trifluorophenyl)urea | oil |
| 434 | 1-(n-Heptyl)-1-[4-(cyclopentyl)benzyl]-3-(2,4-difluorophenyl)urea | oil |
| 435 | 1-(n-Heptyl)-1-[4-(cyclopentyl)benzyl]-3-(4-chloro-2,6-dichlorophenyl)urea | 119–121 |
| 436 | 1-(n-Heptyl)-1-[4-(2-ethylhexyl)benzyl]-3-(2,4-difluorophenyl)urea | oil |
| 437 | 1-(n-Heptyl)-1-[4-(cyclopentyl)benzyl]-3-(2,4,6-trifluorophenyl)urea | solid |
| 438 | 1-(n-Heptyl)-1-[4-(2-ethylbutyl)benzyl]-3-(4-chloro-2,6-dimethylphenyl)urea | oil |
| 439 | 1-(n-Heptyl)-1-[4-(2-methylpentyl)benzyl]-3-(2,4-difluorophenyl)urea | oil |
| 440 | 1-(n-Heptyl)-1-[4-(2-methylpentyl)benzyl]-3-(2,4,6-trifluorophenyl)urea | oil |
| 441 | 1-(n-Heptyl)-1-[4-(2-methylpentyl)benzyl]-3-(4-chloro-2,6-dimethylphenyl)urea | oil |
| 442 | 1-(n-Heptyl)-1-[4-(3-methylpentyl)benzyl]-3-(2,4-difluorophenyl)urea | oil |
| 443 | 1-(n-Heptyl)-1-[4-(3-methylpentyl)benzyl]-3-(2,4,6-trifluorophenyl)urea | oil |
| 444 | 1-(n-Heptyl)-1-[4-(3-methylpentyl)benzyl]-3-(4-chloro-2,6-dimethylphenyl)urea | oil |
| 445 | 1-(n-Heptyl)-1-[4-(cyclobutylmethyl)benzyl]-3-(4-chloro-2,6-dimethylphenyl)urea | solid |
| 446 | 1-(n-Heptyl)-1-[4-(cyclobutylmethyl)benzyl]-3-(2,4-difluorophenyl)urea | oil |
| 447 | 1-(n-Heptyl)-1-[4-(cyclopentylmethyl)benzyl]-3-(2,4,6-trifluorophenyl)urea | solid |
| 448 | 1-(n-Heptyl)-1-[4-(4-cyclopentylmethyl)benzyl]-3-(2,4-difluorophenyl)urea | oil |
| 449 | 1-(n-Heptyl)-1-[4-(cyclobutylmethyl)benzyl)] -3-(2,4,6-trifluorophenyl)urea | solid |
| 450 | 1-(n-Heptyl)-1-[4-(1,5-dimethylhexyl)benzyl]-3-(2,4-difluorophenyl)urea | oil |
| 451 | 1-(n-Heptyl)-1-[4-(1,5-dimethylhexyl)benzyl]-3-(4-chloro-2,6-dimethylphenyl)urea | oil |
| 452 | 1-(n-Heptyl)-1-[4-(1,5-dimethylhexyl)benzyl]-3-(2,4-trifluoromethylphenyl)urea | oil |
| 453 | 1-(n-Heptyl)-1-[4-(cyclopentylmethyl)benzyl]-3-(4-chloro-2,6-dimethylphenyl)urea | 109–111 |
| 454 | 1-(n-Heptyl)-1-[4-(hydroxymethyl)benzyl]-3-(2,4-difluorophenyl)urea | oil |
| 455 | 1-(n-Heptyl)-1-[4-(acetoxymethyl)benzyl]-3-(2,4-difluorophenyl)urea | 65–71 |
| 456 | 1-(n-Heptyl)-1-[4-(isopentyloxy)benzyl]-3-(4-chloro-2,6-dimethylphenyl)urea | 82–85 |
| 457 | 1-(n-Heptyl)-1-[4-(isopentyloxy)benzyl]-3-(2,4-difluorophenyl)urea | oil |
| 458 | 1-(n-Heptyl)-1-[4-(2-methylbutyl)benzyl]-3-(2,4-difluorophenyl)urea | oil |
| 459 | 1-(n-Heptyl)-1-[4-(2-methylbutyl)benzyl]-3-(2,4,6-trifluorophenyl)urea | solid |
| 460 | 1-(n-Heptyl)-1-[4-(2-isopropylthioethyl)benzyl]-3-(4-chloro-2,6-dimethylphenyl)urea | 112–113 |
| 461 | 1-(n-Heptyl)-1-[4-(2-isopropylsulfonylethyl)benzyl]-3-(2,4-difluorophenyl)urea | oil |
| 462 | 1-(n-Heptyl)-1-[4-(2-isopropylsulfonylethyl)benzyl]-3-(4-chloro-2,6-dimethylphenyl)urea | 130–131 |
| 463 | 1-(n-Heptyl)-1-[4-(2,3-dimethylpentyl)benzyl]-3-(2,4-difluorophenyl)urea | oil |
| 464 | 1-(n-Heptyl)-1-[4-(2-isopropylthioethyl)benzyl]-3-(2,4-difluorophenyl)urea | oil |
| 465 | 1-(n-Heptyl)-1-[4-(2-isopropylsulfinylethyl)benzyl]-3-(4-chloro-2,6-dimethylphenyl)urea | oil |
| 466 | 1-(n-Heptyl)-1-[4-(2,3-dimethylpentyl)benzyl]-3-(2,4,6-trifluorophenyl)urea | oil |

TABLE V-continued

| Example | Compound | M.P. °C. |
|---|---|---|
| 467 | 1-(n-Heptyl)-1-[4-(1,2-dimethylpropyl)benzyl]-3-(2,4-difluorophenyl)urea | 32–34 |
| 468 | 1-(n-Heptyl)-1-[4-(1,2-dimethylpropyl)benzyl]-3-(2,4,6-trifluorophenyl)urea | 69–70 |
| 469 | 1-(n-Heptyl)-1-[4-(1,2-dimethylpropyl)benzyl]-3-(4-chloro-2,6-dimethylphenyl)urea | 108–110 |
| 470 | 1-(n-Heptyl)-1-[4-(2,3-dimethylpentyl)benzyl]-3-(4-chloro-2,6-dimethylphenyl)urea | oil |
| 471 | 1-(n-Heptyl)-1-[4-(2-isopropylsulfinylethyl)benzyl]-3-(2,4-difluorophenyl)urea | oil |
| 472 | 1-(n-Heptyl)-1-[4-(isopentyloxymethyl)benzyl]-3-(2,4-difluorophenyl)urea | oil |
| 473 | 1-(n-Heptyl)-1-[4-(isopentyloxymethyl)benzyl]-3-(2,4,6-trifluorophenyl)urea | oil |
| 474 | 1-(n-Heptyl)-1-[4-(isopentyloxymethyl)benzyl]-3-(4-chloro-2,6-dimethylphenyl)urea | oil |

EXAMPLE 475

1-Benzyl-1-(n-butyl)-3-(3-chlorophenyl)urea

A solution of 1.56 g of phenyl chloroformate in 50 ml of ether was added dropwise to a stirred solution of 2.55 g of 3-chloroaniline in 35 ml of ether. The mixture was stirred for one hour at room temperature and then filtered. The filtrate was evaporated and the residue crystallized from hexane to yield phenyl N-(3-chlorophenyl)-carbamate.

A solution of 1.46 g of phenyl N-(3-chlorophenyl)carbamate in 15 ml of tetrahydrofuran was added to a solution of 1.92 g of N-benzyl-n-butylamine in 20 ml of tetrahydrofuran and the mixture stirred under reflux for 24 hours. The mixture was diluted with hexane and the precipitate collected by filtration. Recrystallization from pentane afforded 1-benzyl-1-(n-butyl)-3-(3-chlorophenyl)urea, m.p. 69°–70° C.

EXAMPLE 476

1-Benzyl-1-(n-butyl)-3-(4-carboxyphenyl)urea

A solution of 5.30 g of 1-benzyl-1-(n-butyl)-3-(4-carboethoxyphenyl)urea in 100 ml of ethanol is treated with 25 ml of 1N aqueous sodium hydroxide, stirred under reflux for 16 hours, allowed to cool, acidified with 1N hydrochloric acid, and filtered. The solid is recrystallized from ethanol to yield 1-benzyl-1-(n-butyl)-3-(4-carboxyphenyl)urea as a white solid.

EXAMPLE 477

1-Benzyl-1-(n-butyl)-3-(2-hydroxy-3-chlorophenyl)urea

A solution of 1.73 g of 1-benzyl-1-(n-butyl)-3-(2-methoxy-3-chlorophenyl)urea and 1.0 ml of boron tribromide in 40 ml of methylene chloride was stirred at ambient temperature for 3 days and diluted with water. The organic layer was separated, dried, and evaporated. The residue was crystallized from hexane to yield 1-benzyl-1-(n-butyl)-3-(2-hydroxy-3-chlorophenyl)urea, m.p. 59°–62° C.

EXAMPLE 478

N-(2-Chlorobenzyl)-3-methoxyphenylacetamide

A mixture of 12.5 g of 3-methoxyphenylacetic acid, 21.2 g of 2-chlorobenzylamine, 15.1 g of triethylamine, 19.3 ml of borontrifluoride etherate, and 500 ml of toluene was stirred under reflux for 18 hours using a Dean-Stark moisture trap and allowed to cool. The mixture was extracted with aqueous sodium hydroxide, dilute hydrochloric acid, and water. The remaining organic solution was then evaporated and the residue crystallized from hexane to yield N-(2-chlorobenzyl)-3-methoxyphenylacetamide as a yellow solid, m.p. 89°–91° C.

EXAMPLE 479

N-(n-Butyl)-2-chlorobenzylamine

A solution of 21.2 g of N-(n-butyl)-2-chlorobenzamide in 100 ml of tetrahydrofuran was added with cooling to 200 ml of 1M borane in tetrahydrofuran and the mixture was stirred under reflux for 18 hours, allowed to cool, and treated with 6N hydrochloric acid. The organic solvent was evaporated, and the residue was partitioned between ether and aqueous sodium hydroxide solution. The ether layer was separated, dried, and evaporated. The residue was distilled to yield N-(n-butyl)-2-chlorobenzylamine as a colorless liquid, b.p. 65°–75° C. at 60μ.

EXAMPLE 480

4-Butyl-N-(6-hydroxyphexyl)benzamide

To a stirred solution of 23.5 g of 6-amino-1-hexanol and 30 g of triethylamine in 200 ml of dichloromethane, cooled in an ice bath, was added dropwise a solution of 43.3 g of p-butylbenzoyl chloride in 100 ml of dichloromethane. The mixture was allowed to stir at room temperature for 16 hours. Then the mixture was washed in succession with water, saturated sodium carbonate, water, and finally brine. The organic layer was dried over anhydrous sodium sulfate and evaporated in vacuo. The residue was triturated, filtered, and rinsed with cold hexane and gave 47.5 g of the desired product in 61% yield as a beige solid, m.p. 80°–81° C.

Additional amides (Examples 481–486), which are listed in Table VI, were prepared according to the procedure of Example 480.

TABLE VI

| Example | Amide | Description | MP or BP | % Yield |
|---|---|---|---|---|
| 481 | 4-Butyl-N—[2-(2-hydroxyethoxy)ethyl]-benzamide | Yellow Oil | | 93 |
| 482 | N—Heptyl-2-furancarboxamide | Colorless Liquid | 121° C./0.1 mm | 99 |

TABLE VI-continued

| Example | Amide | Description | MP or BP | % Yield |
|---|---|---|---|---|
| 483 | 4-Butoxy-N—(2-thienylmethyl)benzamide | White Crystals | 128–130° C. | 72 |
| 484 | N—(2-Thienylmethyl)heptanamide | Colorless Solid | 62–63° C. | 82 |
| 485 | N—[(4-Butylphenyl)methyl]-5-(trimethyl-silyl)pentanamide | White Solid | 72–74° C. | 55 |
| 486 | 3,3-Dimethylbutyl-2-thiophenecarboxamide | White Solid | 145–146° C. | 91 |

EXAMPLE 487

6-[[(4-Butylphenyl)methyl]amino]-1-hexanol

To a solution of 45.0 g of the product of Example 1 in 200 ml of tetrahydrofuran, cooled in an ice bath was added dropwise, 325 ml of borane (1M boranetetrahydrofuran complex). The resulting mixture was heated at reflux for 16 hours. The mixture was cooled to room temperature and 57 ml of 6N hydrochloric acid was added dropwise over argon gas. The solvent was evaporated in vacuo. The residue was slurried in water while adding sodium hydroxide pellets until the pH was basic. The aqueous solution was extracted with diethyl ether. The etheral extract was dried over anhydrous sodium sulfate, then evaporated in vacuo, and gave 33.7 g of the desired product in 79% yield, as a yellow oil.

EXAMPLE 488

4-Butyl-N-[5-(trimethylsilyl)pentyl]benzenemethanamine

To a suspension of 2.5 g of lithium aluminum hydride in 100 ml of anhydrous tetrahydrofuran was added dropwise a solution of 5.0 g of N-[(4-butylphenyl)methyl]-5-(trimethylsilyl)pentanamide in tetrahydrofuran. The resulting mixture was heated at reflux for 16 hours. The mixture was cooled, and the complex was decomposed by the cautious portionwise addition of sodium sulfate decahydrate. The mixture was stirred for ½ hour and then filtered. The solid was washed with tetrahydrofuran, and the filtrate was dried with anhydrous magnesium sulfate and filtered. The filtrate was evaporated to dryness and gave 4.53 g of the desired product as a colorless liquid, in 95% yield.

EXAMPLE 489

3,3-Dimethylbutyl-2-thiophenemethanamine

To a solution of 17.0 ml of Vitride ® T [sodium dihydrobis(2-methoxyethoxy)aluminate (70% solution in toluene)] in 50 ml of toluene, was added dropwise a solution of 5.0 g of 3,3-dimethylbutyl-2-thiophene carboxamide in 50 ml of dried tetrahydrofuran. The resulting mixture was heated at reflux for 2 hours, then cooled. The complex was decomposed by adding dropwise 30 ml of 2.5N sodium hydroxide. The mixture was stirred for one hour. The layers were separated and the organic layer was washed with brine, dried over anhydrous magnesium sulfate and filtered. The filtrate was evaporated in vacuo and gave a light brown liquid. Kugelrohr distillation (75° C./0.15 mm of mercury) gave 4.0 g (82% yield) of the desired product.

Additional secondary amines are listed in Table VII and were prepared by the procedures described in Examples 487–489.

TABLE VII

| Example | Example Procedure | Amide Precursor | Amine | Description | MP or BP | % Yield |
|---|---|---|---|---|---|---|
| 490 | 487 | Ex. 482 | N—Heptyl-2-furanmethanamine | Colorless Liquid | 70–75° C./0.08 mm | 67 |
| 491 | 488 | Ex. 485 | 4-Butyl-N—[5-(trimethylsilyl)pentyl]benzenemethanamine | Colorless Liquid |  | 95 |
| 492 | 487 | Ex. 481 | 2-[2-[[(4-Butylphenyl)methyl]amino]ethoxy]-ethanol | Colorless Liquid |  | 83 |
| 493 | 488 | Ex. 484 | N—Heptyl-2-thiophenemethanamine | Colorless Liquid | 90–100° C./0.20 mm | 96 |
| 494 | 488 | Ex. 483 | N—[(4-Butoxyphenyl)methyl]-2-thiophenemethanamine | Colorless Liquid |  | 92 |

EXAMPLE 495

[1-[(4-Butylphenyl)methyl]-3-(2,4-dimethylphenyl)-1-(6-hydroxyhexyl)urea

To a stirred solution of 1.46 g of 2,4-dimethylphenyl isocyanate in 100 ml of hexane was added a solution of 2.63 of 6-[[(4-butylphenyl)methyl]amino]-1-hexanol (prepared as described in Example 489) in 500 ml of hexane. The mixture was stirred at room temperature for 2 hours. Evaporation gave a gum. The gum was purified by chromatography to yield 2.81 g of the desired product as a colorles gum.

Additional ureas and thioureas of the present invention were prepared by the reaction of an appropriate arylisocyanate or arylisothiocyanate with a hereinbefore prepared secondary amine by the method of Example 495. The compounds appear in Table VIII.

TABLE VIII

| Example | Amine Precursor | Product | Description | MP or BP °C. | % Yield |
|---|---|---|---|---|---|
| 496 | Ex. 490 | 1-(2-Furanylmethyl)-1-heptyl-3-(2,4,6-trimethylphenyl)urea | White Solid | 65–67 | 86 |
| 497 | Ex. 490 | 1-(2-Furanylmethyl)-1-heptyl-3-(2,4,6-trichlorophenyl)urea | Yellow Oil | 135–140/0.175 mm | 87 |

TABLE VIII-continued

| Example | Amine Precursor | Product | Description | MP or BP °C. | % Yield |
|---|---|---|---|---|---|
| 498 | Ex. 487 | 1-[(4-Butylphenyl)methyl]-3-(4-chloro-2-methylphenyl)-1-(6-hydroxyhexyl)urea | Colorless Oil | | 58 |
| 499 | Ex. 487 | 1-[(4-Butylphenyl)methyl]-1-(6-hydroxyhexyl)-3-(2,4,5-trimethylphenyl)urea | Colorless Gum | | 63 |
| 500 | Ex. 492 | 1-[(4-Butylphenyl)methyl]-3-(2,4-dimethylphenyl)-1-[2-(2-hydroxyethoxy)ethyl]urea | Colorless Gum | | 46 |
| 501 | Ex. 492 | 1-[(4-Butylphenyl)methyl]-1-[2-(2-hydroxyethoxy)ethyl]-3-(2,4,5-trimethylphenyl)urea | White Solid | 84–86 | 89 |
| 502 | Ex. 493 | 1-Heptyl-1-(2-thienylmethyl)-3-(2,4,5-trimethylphenyl)urea | White Solid | 84–85 | 94 |
| 503 | Ex. 493 | 1-Heptyl-1-(2-thienylmethyl)-3-(2,4,6-trichlorophenyl)urea | White Solid | 72–73 | 72 |
| 504 | Ex. 494 | 1-[(4-Butoxyphenyl)methyl]-1-(2-thienylmethyl)-3-(2,4,5-trimethylphenyl)urea | White Solid | 114–115 | 99 |
| 505 | Ex. 487 | 1-[(4-Butylphenyl)methyl]-1-(6-hydroxyhexyl)-3-(2,4,6-trichlorophenyl)urea | Light Brown Oil | | 65 |
| 506 | Ex. 491 | 1-[(4-Butylphenyl)methyl]-3-(4-chloro-2-methylphenyl)-1-[5-(trimethylsilyl)pentyl]urea | Colorless Oil | 165–170/0.080 mm | 77 |
| 507 | Ex. 491 | 1-[(4-Butylphenyl)methyl]-3-(2,4-difluorophenyl)-1-[5-(trimethylsilyl)pentyl]urea | Colorless Oil | 165/0.080 mm | 82 |
| 508 | Ex. 489 | 3-(2,4-Difluorophenyl)-1-(3,3-dimethylbutyl)-1-(2-thienylmethyl)urea | Colorless Liquid | 75/0.150 mm | 73 |
| 509 | Ex. 489 | 3-(4-Chloro-2-methylphenyl)-1-(3,3-dimethylbutyl)-1-(2-thienylmethyl)urea | White Solid | 111–113 | 64 |
| 510 | Ex. 489 | 1-(3,3-Dimethylbutyl)-1-(2-thienylmethyl)-3-(2,4,6-trichlorophenyl)urea | White Solid | 118–120 | 91 |

Other ureas and thioureas which may be prepared by the method described in Example 495 include:
1-[(4-Butylphenyl)methyl]-3-[(2-methoxy-5-methyl)-phenyl]-1-[5-(trimethylsilyl)pentyl]urea
1-[(4-Butylphenyl)methyl]-3-[(4-carboethoxy-2-methyl)phenyl]-1-[5-(trimethylsilyl)pentyl]urea
1-[(4-n-Butylphenyl)methyl]-3-[(4-carboxy-2-methyl)-phenyl]-1-[5-(trimethylsilyl)pentyl]urea

EXAMPLE 511

Phenyl-N-(2,4-difluorophenyl)carbamate

To a solution of 1.94 g of 2,4-difluoroaniline in 20 ml of toluene was added dropwise 1.29 g of phenyl chloroformate. The mixture was stirred for 15 minutes, washed with three 10 ml portions of water, dried over anhydrous sodium sulfate, and filtered through a pad of diatomaceous earth. The filtrate was evaporated in vacuo to give an oil which solidified on cooling. The solid was crystallized from hexane to give 1.73 g of the desired product as pale tan crystals in 93% yield, mp 82°–84° C.

EXAMPLE 512

1-[(4-Butylphenyl)methyl]-3-(2,4-difluorophenyl)-1-(6-hydroxyhexyl)urea

A mixture of 1.58 g of 6-[[(4-butylphenyl)-methyl]amino]-1-hexanol and 1.5 g of phenyl-N-(2,4-difluorophenyl)carbamate in 40 ml of toluene was heated at reflux for 5 hours. The reaction mixture was cooled and allowed to stand at room temperature for 16 hours. The solution was washed with 3N aqueous hydrochloric acid, brine, 1N aqueous sodium hydroxide and brine again, then was dried over anhydrous magnesium sulfate and filtered. The filtrate was evaporated in vacuo and gave a yellow oil. The oil was treated by preparative high pressure liquid chromatography and gave 0.93 g (37%) of the desired product as a colorless oil.

EXAMPLE 513

Phenyl[(4-butylphenyl)methyl][6-hydroxyhexyl]carbamate

To a stirred solution of 7.26 g of 6-[[(4-butylphenyl)-methyl]amino]-1-hexanol in 50 ml of toluene was added a solution of 2.16 g of phenyl chloroformate in 20 ml of toluene, with the immediate precipitation of a white solid. The resulting mixture was stirred at room temperature for 24 hours. The mixture was filtered, and the filter was washed with toluene. The combined filtrate and wash was evaporated in vacuo and gave a colorless oil. The oil was Kugelrohr distilled and gave 3.5 g of the desired product in 66% yield as a colorless oil, bp 180°–195° C./0.06 mm of mercury.

EXAMPLE 514

5-(Trimethylsilyl)pentanoic acid

Preparation of Grignard reagent:
To a suspension of 1.58 g of magnesium turnings in 7.0 ml of freshly distilled tetrahydrofuran (distilled over benzophenone and sodium metal) was added about 2.0 ml of bromomethyltrimethylsilane under argon. A few crystlas of iodine were added and the mixture was heated with a hot air gun. The reaction began immediately and an additional amount of bromomethyltrimethylsilane (for a total of 10.03 g) was added dropwise over a 20 minute period. The mixture was stirred and heated at an oil bath temperature of 70°–80° C. for an additional 3 hours, then cooled at room temperature and allowed to stand.

In another flask a solution of 9.02 g of 4-bromobutyric acid in 30 ml of dry, freshly distilled, tetrahydrofuran was stirred and cooled at −30° C. under argon, the 19.0 ml of methyl magnesium chloride was added to the solution while maintaining the temperature at −20° C. The mixture was stirred at −20° C. for 10 minutes, then a solution of dilithium tetrachlorocuprate (prepared by dissolving 85.4 mg of lithium chloride and 173 mg of cupric chloride in 8.0 ml of tetrahydrofuran) was added to the reaction mixture, and stirring was continued for 5 minutes longer at −20° C. Then the hereinabove prepared Grignard reagent in 7.0 ml of tetrahydrofuran (kept in solution by warming) was added dropwise at −20° C. The resulting mixture was stirred at −20° C. for one hour more, then at ambient temperature for 16 hours.

The reaction mixture was then poured into a mixture of ethyl acetate:10% sulfuric acid (200 ml:200 ml) and stirred for 5 minutes. The two layers were separated and the organic layer was washed three times with brine, dried over anhydrous magnesium sulfate and filtered. The volatiles were evaporated in vacuo to leave a brown liquid. The liquid was distilled using a Vigreux column and an oil bath temperature of 150°–160° C. for the third fraction which gave 7.5 g of the desired product (bp 139°–139.5° C./10 mm) as a pinkish liquid (80% yield).

EXAMPLE 515

1-[(4-Butylphenyl)methyl]-1-[6-[(methylsulfonyl)oxy]hexyl]-3-[(2,4,5-trimethylphenyl)methyl]urea To a cooled solution (0°–5° C.) of 10.0 g of 1-[(4-butylphenyl)methyl]-1-6-(hydroxyhexyl)-3-(2,4,5-trimethylphenyl)urea and 7.3 ml (5.3 g) of triethylamine in 125 ml of dichloromethane was added dropwise a solution of 2.4 ml of methanesulfonyl chloride in 25 ml of dichloromethane. The resulting solution was gradually warmed to room temperature and stirred for 3 hours. The mixture was poured into ice-water. The organic layer was separated and washed in succession with 10% aqueous hydrochloric acid, water, a saturated aqueous solution of sodium bicarbonate, and brine. The organic solution was then dried over anhydrous magnesium sulfate and filtered. The filtrate was evaporated to dryness to yield 10.4 g (88%) of the desired product as a light brown oil.

EXAMPLE 516

1-[(4-Butylphenyl)methyl]-1-[6-(methylsulfonyloxy)hexyl]-3-(2,4,6-trichlorophenyl)urea To a cooled solution (0°–5° C.) of 4.0 g of 1-[(4-butylphenyl)methyl]-1-(6-hydroxyhexyl)-3-(2,4,6-trichlorophenyl)urea and 2.6 ml of triethylamine in 90 ml of dichloromethane was added dropwise a solution of 0.8 ml of methanesulfonyl chloride in 10 ml of dichloromethane. The resulting solution was allowed to come to room temperature and was stirred for 16 hours. The procedure of Example 515 was continued and gave 4.5 g of the desired product as a light yellow oil in 97% yield.

EXAMPLE 517

1-[(4-Butylphenyl)methyl]-3-(4-chloro-2-methylphenyl)-1-[6-[(methylsulfonyl)oxy]hexyl]urea To a cooled solution (0°–5° C.) of 5.24 g of 1-[(4-butylphenyl)methyl]-3-(4-chloro-2-methylphenyl)-1-(6-hydroxyhexyl)urea and 4.0 ml of triethylamine in 65 ml of dichloromethane was added dropwise a solution of 1.2 ml of methanesulfonyl chloride in 10 ml of dichloromethane. The resulting solution was gradually warmed to room temperature, then was stirred for 16 hours. The procedure of Example 515 was continued and gave 6.0 g of the desired product as a light brown oil in 97% yield.

EXAMPLE 518

1-[(4-Butylphenyl)methyl]-1-(6-cyanohexyl)-3-(2,4,5-trimethylphenyl)urea

A mixture of 2.0 g of 1-[(4-butylphenyl)methyl]-1-[6-[(methylsulfonyl)oxy]hexyl]-3-[(2,4,5-trimethylphenyl)methyl]urea, 0.5 g of sodium cyanide and 5.0 ml of dimethyl sulfoxide was heated at an oil bath temperature of 60°–70° C. for 1½ hours. The mixture was cooled and poured into ice-water. The mixture was extracted with ether. The etheral layer was separated, washed with brine, dried over magnesium sulfate, and filtered. The filtrate was evaporated to dryness to yield 1.45 g (84%) of the desired product as a light brown oil.

EXAMPLE 519

1-[(4-Butylphenyl)methyl]-1-(6-cyanohexyl)-3-(2,4,6-trichlorophenyl)urea

A mixture of 2.2 g of N-[(4-butylphenyl)methyl]-N-[6-(methylsulfonyloxy)hexyl]-N-(2,4,6-trichlorophenyl)-urea, 0.5 g of sodium cyanide, and 3.0 ml of dried dimethyl sulfoxide was heated at an oil bath temperature of 60°–70° C. for 20 hours. The mixture was poured into water and extracted with dichloromethane. The procedure of Example 518 was continued and gave 1.65 g (85% yield) of the desired product as a light brown oil.

EXAMPLE 520

1-[(4-Butylphenyl)methyl]-3-(4-chloro-2-methylphenyl)-1-(6-cyanohexyl)urea

A mixture of 2.0 g of 1-[(4-butylphenyl)methyl]-3-(4-chloro-2-methylphenyl)-1-[6-[(methylsulfonyl)oxy]hexyl]urea, 0.5 g of sodium cyanide, and 3.0 ml of dimethyl sulfoxide was heated at an oil bath temperature of 60°–70° C. for 16 hours. The mixture was poured into water and extracted with dicholormethane. The procedure of Example 518 was continued and gave 1.5 g (88% yield) of the desired product as a brown oil.

EXAMPLE 521

1-[(4-Butylphenyl)methyl]-1-(6-chlorohexyl)-3-(2,4,5-trimethylphenyl)urea

A mixture of 2.0 g of 1-[(4-butylphenyl)methyl]-1-[6-[(methylsulfonyl)oxy]hexyl]-3-[(2,4,5-trimethylphenyl)methyl]urea, 0.74 g of potassium chloride, and 4.0 ml of dimethyl sulfoxide was heated at an oil bath temperature of 60° C. for 12 hours. The mixture was cooled and poured into ice-water. The mixture was extracted with ether. The ether layer was washed with brine, dried over anhydrous magnesium sulfate, and filtered. The filtrate was evaporated in vacuo to yield 1.5 g of a light brown oil. The oil was purified by chromatography to yield 1.2 g of the desired product (68% yield) as a colorless oil.

EXAMPLE 522

1-[(4-Butylphenyl)methyl]-1-(6-chlorohexyl)-3-(2,4,6-trichlorophenyl)urea

A mixture of 1.9 g of 1-[(4-butylphenyl)methyl]-1-[6-[(methylsulfonyl)oxy]hexyl]-3-(2,4,6-trichlorophenyl)]-urea, 0.6 g of potassium chloride, and 3.0 ml of dried dimethyl sulfoxide was heated at an oil bath temperature of 60°-70° C. for 20 hours. The extraction and chromatography procedures of Example 521 were followed to give 1.1 g of the desired product as a colorless oil.

EXAMPLE 523

1-[(4-Butylphenyl)methyl]-1-(6-chlorohexyl)-3-(4-chloro-2-methylphenyl)urea

A mixture of 2.0 g of 1-[(4-butylphenyl)methyl]-3-(4-chloro-2-methylphenyl)-1-[6-[(methylsulfonyl)oxy]-hexyl]urea, 0.74 g of potassium chloride, and 3.0 ml of dimethyl sulfoxide was heated at an oil bath temperature of 60°-80° C. for 16 hours. The mixture was diluted with water and extracted with dichloromethane. The organic layer was washed with three 40 ml portions of brine, dried over anhydrous magnesium sulfate and filtered. The filtrate was evaporated in vacuo to yield 1.5 g of a brown oil. The oil was purified by chromatography to yield 1.5 g of the desired product as a light yellow oil in 86% yield.

EXAMPLE 524

1-[(4-Butylphenyl)methyl]-3-(2-hydroxy-5-methylphenyl)-1-8 5-(trimethylsilyl)pentyl]urea To an ice cold solution of 10 ml of borontribromide in dichloromethane is added dropwise a solution of 2.34 g of 1-[(4-butylphenyl)methyl]-3-[(2-methoxy-5-methyl)-phenyl]-1-[5-(trimethylsilyl)pentyl]urea in 20 ml of dichloromethane. The mixture is allowed to stir at room temperature for 24 hours, then is diluted with 50 ml of water and stirred for 3 hours. Two layers are separated. The organic layer is washed with brine, dried over anhydrous magnesium sulfate and filtered. The filtrate is evaporated to dryness to yield an oil. The oil is purified by Kugelrohr distillation to give the desired product.

EXAMPLE 525

1-[(4-Butylphenyl)methyl]-3-[(4-carboxy-2-methyl)-phenyl]-1-[5-(trimethylsilyl)pentyl]urea A solution of 1.28 g of 1-[(4-butylphenyl)methyl]-3-](4-carboethoxy-2-methyl)phenyl]-1-[5-(trimethylsilyl)-pentyl]urea in 30 ml of ethanol is treated with 5.0 ml of 1N sodium hydroxide. The resulting solution is stirred under reflux for 16 hours. The mixture is cooled and acidified with 1N hydrochloric acid. The precipitated solid is collected by filtration, washed with water, and dried. The desired product is crystallized from ethanol.

EXAMPLE 526

4-Butylbenzamide

To a stirred solution of 200 ml of aqueous ammonium hydroxide was added dropwise 35 ml of 4-butylbenzoyl chloride. The resulting mixture was stirred at room temperature for several hours. The white solid was collected by filtration, washed with water, then hexane, and dried in vacuo at 60° C. to give 33.4 g (99% yield) of the desired product, mp 135°-136° C.

EXAMPLE 527

4-Butylbenzenemethanamine

To a suspension of 15 g of lithium aluminum hydride in 200 ml of anhydrous ethyl ether under argon was added, at room temperature, a solution of 32. 0 g of 4-butylbenzamide in 200 ml of freshly distilled tetrahydrofuran. The resulting mixture was stirred at room temperature for one hour and then heated at reflux for 20 hours. The mixture was cooled and sodium sulfate decahydrate was cautiously added portionwise to the mixture until it was colorless. The mixture was stirred for 30 minutes. The mixture was filtered and the filter was washed with ether. The filtrate was evaporated in vacuo to yield 29 g (99% yield) of a liquid. The liquid was distilled by Kugelrohr distillation, bp 85° C./0.070 mm of mercury, to give the desired product as a colorless liquid.

EXAMPLE 528

N-Heptyl-4-n-butylbenzamide

To a cold solution of 16 g of n-heptylamine and 29.0 ml of triethylamine in 300 ml of methylene chloride was added dropwise a solution of 27.4 g of 4-butylbenzoylchloride in 100 ml of methylene chloride. The resulting mixture was stirred at room temperature for 4½ hours and diluted with water. The organic layer was washed with 1N sodium hydroxide, brine, dried, and evaporated. The residual solid was recrystallized from hexane to yield N-heptyl-4-n-butylbenzamide, mp 37°-38° C.

EXAMPLE 529

N-Heptyl-4-n-butylbenzenemethanamine

A solution of 38.0 g of N-heptyl-4-n-butylbenzamide and 280 ml of borane-tetrahydrofuran complex in 120 ml of anhydrous tetrahydrofuran was refluxed for 18 hours, allowed to cool, and treated with 6N hydrochloric acid. The organic solvent was evaporated and the residue was partitioned between ether and aqueous sodium hydroxide solution. The ether layer was separated, dried, and evaporated. The residue was distilled to yield N-heptyl-4-n-butylbenzenemethanamine as a colorless liquid, bp 115° C. at 80μ.

EXAMPLE 530

1-[(4-Butylphenyl)methyl]-1-(n-heptyl)-3-[2,4-difluorophenyl]urea

A solution of 1.55 g of 2,4-difluorophenylisocyanate in hexane was added to a solution of 2.61 g of N-heptyl-4-butylbenzenemethanamine in 15 ml of hexane and the solution was stirred at room temperature for 4 hours, then evaporated. The residual oil was distilled to yield 1-[(4-butylphenyl)methyl]-1-(n-heptyl)-3-[2,4-difluorophenyl]urea as a colorless oil, bp 160°-165° C./120μ.

EXAMPLE 531

N-[3,3-Dimethylbutyl]-4-n-butylbenzamide

To a solution of 4.94 g of 4-butylbenzoylchloride in 20 ml of methylene chloride was added dropwise a solution of 2.53 g of 3,3-dimethylbutylamine and 5.1 g of triethylamine in 80.0 ml of methylene chloride. The resulting mixture was stirred at room temperature for 18 hours. The mixture was diluted with water, and the organic layer was washed with 6N hydrochloric acid, water, 2N sodium hydroxide, brine, dried, and evaporated to dryness to yield an oil which solidified on standing. The solid was triturated with hexane, collected by filtration, and dried to yield N-[3,3-dimethylbutyl]-4-n-butylbenzamide as a white solid, mp 70°–71° C.

EXAMPLE 532

N-[3,3-Dimethylbutyl]-4-n-butylbenzenemethanamine

A solution of 7.5 g of N-[3,3-dimethylbutyl]-4-n-butylbenzenemethanamine in 40 ml of tetrahydrofuran was added dropwise to a suspension of 3.3 g of lithium aluminium hydride in 80 ml of tetrahydrofuran. The resulting mixture was refluxed for 18 hours, cooled, and the complex was decomposed by adding sodium sulfate decahydrate portionwise until a colorless mixture was obtained. The mixture was stirred for an additional half hour, filtered, and the filtrate was evaporated to dryness to yield a liquid. The liquid was distilled to yield N-[3,3-dimethylbutyl]-4-n-butylbenzenemethanamine as a colorless liquid, bp 80°–90° C. at 80μ.

EXAMPLE 533

Phenyl-N-(4-chloro-2,6-dimethylphenyl)carbamate

A solution of 2.56 g of phenyl chloroformate in 20 ml of toluene was added to a cold solution of 2.47 g of 4-chloro-2,6-dimethylaniline and 2.4 ml of N,N-dimethylaniline in 80 ml of toluene. The resulting mixture was stirred at room temperature for 1½ hours and then diluted with water. The organic layer was washed with 3N hydrochloric acid, brine, dried, and evaporated. The residual solid was crystallized from ethylacetate:-hexane to yield phenyl-N-(4-chloro-2,6-dimethylphenyl)carbamate, mp 158°–160° C.

EXAMPLE 534

1-[(4-Butylphenyl)methyl]-1-[3,3-dimethylbutyl]-3-[4-chloro-2,6-dimethylphenyl]urea A solution of 825 mg of phenyl-N-(4-chloro-2,6-dimethylphenyl]carbamate and 740 mg of N-[3,3-dimethylbutyl]-4-n-butylbenzenemethanamine in 40 ml of toluene was refluxed for 1 hour, cooled, and the solution was washed with 1N sodium hydroxide, brine, dried, and evaporated to dryness to yield a solid. The solid was recrystallized from hexane to yield 1-[(4-butylphenyl)methyl]-1-[3,3-dimethylbutyl]-3-[4-chloro-2,6-dimethylphenyl]urea as a white solid, mp 138°–139° C.

EXAMPLE 535 p-Neopentylbenzoic acid

To a cooled suspension of 43.0 g of anhydrous aluminum chloride in 250 ml of methylene chloride was added 40.0 g of oxalyl chloride over a period of 25 minutes. The resulting mixture was stirred for 5 minutes and then 43.2 g of neopentylbenzene was added dropwise maintaining a temperature of 0°–50° C. over a period of 35 minutes. The dark red mixture was stirred at an ambient temperature and then heated slowly to reflux for 3 hours, cooled, and poured into a mixture of 250 g of ice and 188 ml of concentrated hydrochloric acid. The mixture was stirred for ½ hours, and two layers were separated. The aqueous layer was extracted with methylene chloride and the combined organic layers were evaporated to yield a brown oily residue. The residue was heated and stirred under reflux with 200 ml of 10N sodium hydroxide, 150 ml of water, and 250 ml of ethyl alcohol for 20 minutes, cooled, and the mixture was extracted with ether. The aqueous layer was acidified with concentrated hydrochloric acid and stirred for 1 hour. The solid was collected by filtration, washed with water, dissolved in ethyl acetate, the aqueous layer was discarded, dried and evaporated to yield a solid. The solid was crystallized from acetone to yield p-neopentylbenzoic acid as a beige solid, mp 191°–193° C.

EXAMPLE 536

N-(3,3-Dimethylbutyl)-4-(2,2-dimethylpropyl)benzamide

To a cold solution of 5.26 g of 3,3-dimethylbutylamine and 21.0 ml of triethylamine in 180 ml of methylene chloride was added dropwise a solution of p-neopentylbenzoylchloride in 20 ml of methylene chloride. The resulting mixture was stirred at room temperature for 5 hours and diluted with water. The organic layer was washed with 3N hydrochloric acid, water, 1N sodium hydroxide, brine, dried, and evaporated to yield a solid. The solid was recrystallized from ethylacetate:-hexane to yield N-(3,3-dimethylbutyl)-4-(2,2-dimethylpropyl)benzamide as a beige solid, mp 124°–126° C.

EXAMPLE 537

N-(3,3-Dimethylbutyl)-4-(2,2-dimethylpropyl)benzenemethanamine

A solution of 13.0 g of N-(3,3-dimethylbutyl)-4-(2,2-dimethylpropyl)benzenemethanamine in 50 ml of tetrahydrofuran was added dropwise to a suspension of 6.0 g of lithium aluminum hydride in 200 ml of tetrahydrofuran and the resulting mixture was heated to reflux for 18 hours, then cooled. The mixture was decomposed by adding sodium sulfate decahydrate portionwise until a colorless mixture was obtained. The mixture was stirred for an additional half hour, filtered, and the filtrate was evaporated to yield an oil. The oil was distilled to yield N-(3,3-dimethylbutyl)-4-(2,2-dimethylpropyl)benzenemethanamine as a colorless oil, bp 100°–110° C. at 100μ.

EXAMPLE 538

1-[3,3-Dimethylbutyl]-1-[[4-(2,2-dimethylpropyl)phenyl]methyl]-3-[4-chloro-2,6-dimethylphenyl]urea A solution of 825 mg of phenyl-N-(4-chloro-2,6-dimethylphenyl)carbamate and 782 mg of N-(3,3-dimethylbutyl)-4-(2,2-dimethylpropyl)benzenemethanamine in 40 ml of toluene was heated to reflux for 1 hour, cooled, and the solution was washed with 1N sodium hydroxide, brine, dried, and evaporated to dryness to yield a solid. The solid was recrystallized from hexane to yield 1-[3,3-dimethylbutyl[-1-[[4-(2,2-dimethylpropyl)phenyl]methyl]-3-]4-chloro-2,6-dimethylphenyl]urea as a white solid, mp 148°–150° C.

I claim:

1. A method of reducing the cholesterol ester content of an arterial wall, inhibiting atherosclerotic lesion development, and/or treating hyperlipidemia in a mammal in need of such treatment which comprises administering to said mammal an effective amount of a compound of the formula:

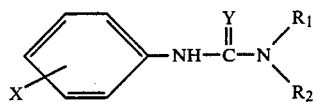

wherein X represents at least one substituent selected from the group consisting of $(C_1-C_4)$alkyl, $(C_1-C_4)$alkenyl, $(C_1-C_4)$alkynyl, phenoxy, mercapto, amino, $(C_1-C_4)$alkylamino, di$(C_1-C_4)$alkylamino, halo, trihalomethyl, $(C_1-C_4)$alkanoyl, benzoyl, $(C_1-C_4)$alkanamido, haloacetamido, nitro, cyano, carboxy, $(C_1-C_4)$carboalkoxy, carbamoyl, sulfamyl, methylenedioxy, phenyl, ortho-phenylene, tolyl, benzyl, halobenzyl, methylbenzyl; Y is selected from the group consisting of oxygen and sulfur; $R_1$ and $R_2$ are different and are independently selected from the group consisting of $(C_4-C_{12})$alkyl, $(C_4-C_{12})$alkenyl, $(C_4-C_{12})$alkynyl, $C_4-C_{12}$ cycloalkylalkyl, $(C_7-C_{14})$aralkyl, and $(C_7-C_{14})$aralkyl in which an aromatic ring bears at least one substituent selected from the group consisting of $(C_1-C_{10})$alkyl, $(C_1-C_{10})$alkoxy, phenoxy, benzyloxy, methylenedioxy, $(C_1-C_4)$alkylthio, phenyl, halo, trihalomethyl, adamantyl, $(C_1-C_4)$carboalkoxy and nitro.

2. A method as recited in claim 1 wherein Y is oxygen.

3. A method as recited in claim 2 wherein X represents at least two $(C_1-C_4)$alkyl substituents.

4. A method as recited in claim 2 wherein X represents at least one halo substituent.

5. A method as recited in claim 2 wherein $R_1$ is $(C_7-C_{14})$aralkyl bearing a $(C_1-C_{10})$alkyl substituent and $R_2$ is $(C_4-C_{12})$alkyl.

6. A method as recited in claim 2 wherein $R_1$ is 4-(2,2-dimethylpropyl)phenylmethyl and $R_2$ is $(C_4-C_{12})$alkyl.

7. A method as recited in claim 2 wherein X represents at least one substituent selected from the group consisting of $(C_1-C_4)$alkyl and halo.

8. A method as recited in claim 2 wherein the compound is 1-(n-heptyl)-1-[4(n-butyl)benzyl]-3-(2-,4-difluorophenyl)urea.

9. A method as recited in claim 2 wherein the compound is 1-(3,3-dimethylbutyl-1-[4-(4-(n-butyl)benzyl]-3-(4-chloro-2,6-dimethylphenyl)urea.

10. The method as recited in claim 2 wherein the compound is 1-(3,3-dimethylbutyl)-1-[4-(2,2-dimethylpropyl)-benzyl]-3-(4-chloro-2,6-dimethylphenyl)urea.

11. A method as recited in claim 2 wherein the compound is 1-(n-heptyl)-1-[4-(2,2-dimethylpropyl)phenylmethyl]-3-(2,4-difluorophenyl)urea.

* * * * *